(12) United States Patent
Sletten et al.

(10) Patent No.: US 12,187,848 B2
(45) Date of Patent: Jan. 7, 2025

(54) COMPOSITIONS AND METHODS FOR CELLULAR DELIVERY

(71) Applicant: The Regents of the University of California, Oakland, CA (US)

(72) Inventors: Ellen M. Sletten, Los Angeles, CA (US); Daniel A. Estabrook, Los Angeles, CA (US); John O. Chapman, Auburn, AL (US)

(73) Assignee: The Regents of the University of California, Oakland, CA (US)

( * ) Notice: Subject to any disclaimer, the term of this patent is extended or adjusted under 35 U.S.C. 154(b) by 176 days.

(21) Appl. No.: 17/612,931

(22) PCT Filed: May 20, 2020

(86) PCT No.: PCT/US2020/033730
§ 371 (c)(1),
(2) Date: Nov. 19, 2021

(87) PCT Pub. No.: WO2020/236894
PCT Pub. Date: Nov. 26, 2020

(65) Prior Publication Data
US 2022/0227937 A1 Jul. 21, 2022

Related U.S. Application Data

(60) Provisional application No. 62/850,514, filed on May 20, 2019.

(51) Int. Cl.
*A61K 47/59* (2017.01)
*C08G 73/02* (2006.01)

(52) U.S. Cl.
CPC .......... *C08G 73/0233* (2013.01); *A61K 47/59* (2017.08)

(58) Field of Classification Search
CPC ........................... C08G 73/0233; A61K 47/59
USPC ..................................................... 514/772.7
See application file for complete search history.

(56) References Cited

U.S. PATENT DOCUMENTS 3,864,320 A * 2/1975 Rolker ................. C08G 63/916
525/437
2015/0307718 A1* 10/2015 Colak .................... A01N 55/00
524/547

FOREIGN PATENT DOCUMENTS

| EP | 2674664 A2 | 12/2013 | |
| WO | WO-2009156180 A2 * | 12/2009 | ............. A01N 25/04 |
| WO | WO-2020/236894 A1 | 11/2020 | |

OTHER PUBLICATIONS

Luxenhofer et al Biomaterials, 2010, 31, 49-72-49-79 (Year: 2010).*
Luxenhofer Macromolecules, 2006, 39, 3509-3516 (Year: 2006).*
Fustin et al., "Multiple micellar morphologies from tri- and tetrablock copoly (2-oxazoline)s in binary water-ethanol mixtures," Journal of Polymer Science Part A: Polymer Chemistry, 48(14):3095-3102 (2010).
Kolouchova et al., "Self-assembled thermoresponsive polymeric nanogels for 19F MR imaging," Biomacromolecules, 19(8):3515-3524 (2018).
Kourti et al., "Block copolymers based on 2-methyl- and 2-phenyl-oxazoline by metallocene-mediated cationic ring-opening polymerization: synthesis and characterization," Polymer Chemistry, 7(16):2821-2835 (2016).
Miyamoto et al., "Spontaneous vinyl polymerization of 2-vinyl-2-oxazolines," Macromolecules, 18(9):1641-1648 (1985).
Shieh et al., "Reduced skin photosensitivity with meta-tetra(hydroxyphenyl) chlorin-loaded micelles based on a poly (2-ethyl-2-oxazoline)-b-poly(d,l-lactide) diblock copolymer in vivo," Molecular Pharmaceutics, 7(4):1244-1253 (2010).
Trutzschler et al., "One-pot synthesis of block copolymers by a combination of living cationic and controlled radical polymerization," Macromolecular Rapid Communications, 40(1):1800398 (2019).
Estabrook et al., "Macromolecular crowding as an intracellular stimulus for responsive nanomaterials", Journal of the American Chemical Society 144.37: 16792-16798 (2022).
Extended European Search Report for Application No. EP 20810638.5 dated Apr. 24, 2023.
Wilson et al., "Poly(2-oxazoline)-based micro- and nanoparticles: A review," European Polymer Journal 88: pp. 486-515 (2016).
Brazel et al., "Pulsatile local delivery of thrombolytic and antithrombotic agents using poly (N-isopropylacrylamide-co-methacrylic acid) hydrogels," Journal of Controlled Release, 39(1):57-64 (1996).
Cabral et a., "Block copolymer micelles in nanomedicine applications," Chemical Reviews, 118(14):6844-6892 (2018).
CAS Registry No. 101-43-9 (Nov. 15, 1984).
CAS Registry No. 1393882-74-0 (Sep. 11, 2012).
CAS Registry No. 1427005-74-0 (Apr. 3, 2013).
CAS Registry No. 158820-10-1 (Nov. 16, 1984).
CAS Registry No. 2495-35-4 (Nov. 16, 1984).
CAS Registry No. 25085-83-0, retrieved online <https://polymerdatabase.com/polymers/polybenzylmethacrylate.html>: Database Accession: Jun. 28, 2020.
CAS Registry No. 25104-37-4 (Nov. 16, 1984).
CAS Registry No. 25322-68-3 (Nov. 16, 1984).
CAS Registry No. 25822-66-6 (Nov. 16, 1984).
CAS Registry No. 25988-53-8 (Nov. 16, 1984).
CAS Registry No. 26100-51-6 (Nov. 16, 1984).
CAS Registry No. 26124-68-5 (Nov. 16, 1984).
CAS Registry No. 27251-32-7 (Nov. 16, 1984).
CAS Registry No. 27458-65-7 (Nov. 16, 1984).
CAS Registry No. 28825-60-7 (Nov. 16, 1984).
CAS Registry No. 30551-89-4 (Nov. 16, 1984).
CAS Registry No. 9002-89-5 (Nov. 16, 1984).
CAS Registry No. 9003-07-0 (Nov. 16, 1984).
CAS Registry No. 9003-09-2 (Nov. 16, 1984).

(Continued)

*Primary Examiner* — Yevgeny Valenrod
(74) *Attorney, Agent, or Firm* — Foley Hoag LLP; David P. Halstead; Alexander J. Chatterley

(57) ABSTRACT

Disclosed herein are amphiphilic polymers and hierarchical structures (e.g., emulsions) comprising said polymer. Also disclosed herein are methods of using the polymers and hierarchical structure disclosed herein.

20 Claims, 12 Drawing Sheets

(56) References Cited

OTHER PUBLICATIONS

CAS Registry No. 9003-28-5 (Nov. 16, 1984).
CAS Registry No. 9003-32-1 (Nov. 16, 1984).
CAS Registry No. 9003-63-8 (Nov. 16, 1984).
CAS Registry No. 9011-14-7 (Nov. 16, 1984).
CAS Registry No. 925-60-0 (Nov. 16, 1984).
ChEBI Database ID: 53589 retrieved online <https://www.ebi.ac.uk/chebi/searchld.do?chebild=53589>: Last modified Mar. 16, 2012.
Chung et al., "thermo-responsive drug delivery from polymeric micelles constructed using block copolymers of poly (N-isopropylacrylamide) and poly (butymethacrylate)," Journal of Controlled Release, 62(1-2):115-127 (1999).
Estabrook et al., Controlling nanoemilsion surface chemistry with poly (2-oxazoline) amphiphiles, Chemical Science, 10(14):3994-4003 (2019).
Filippov et al., "Block and gradient copoly(2-oxazoline)micelles: strikingly different on the inside," Journal of Physical Chemistry Letters, 8(16):3800-3804 (2017).
Foreman et al., "Gelation of amphiphilic lipopolymers at the air-water interface: 2D analogue to 3D gelation of colloidal systems with grafted polymer chains," Langmuir, 19(2):326-332 (2003).
Glassner et al., "Poly(2-oxazoline)s: A comprehensive overview of polymer structures and their physical properties," Polym. Int. 67:32-45 (2017).
Hoogenboom et al., "Microwave-assisted synthesis and properties of a series of poly(2-alkyl-2-oxazoline)s," Des. Mono. Polym. 8(6):659-671 (2005).
International Search Report and Written Opinion for International Application No. PCT/US2020/033730 dated Jul. 29, 2020.
Ivanova et al., "Micellar structures of hydrophilic/lipophilic/fluriphilic poly(2-oxazoline) diblock copolymers in water," Macromolecular Chemistry and Physics, 209(21):2248-2258 (2008).
Jaksh et al., "Amphiphilic triblock copolymers from poly(2-oxazoline) with different hydrophobic blocks: changes of the mocellar structures upon addition of a strongly hydrophobic cancer drug," Macromolecular Chemistry and Physics, 217(13):1448-1456 (2016).
Krieg et al., "Block copolymers of poly(2-oxazoline)s and poly(meth)acrylates: a crossover between cationic ring-opening polymerization (CROP) and reversuble addition-fragmentation chain transfer (RAFT)," ACS Macro Letters, 1(6):776-779 (2012).
Legros et al., "Cyrstalisation-driven self-assembly of poly (2-isopropyl-2-oxazoline)-block-poly (2-methyl-2-oxazoline) above the LCST," Soft Matter, 11(17): 8 pages (2015).
Legros, "Engineering of poly(2-oxazoline)s for potential use in biomedical applications," Ph.D Thesis presented to the University of Waterloo: 242 pages (2015).
Luxenhofer et al., "Poly(2-oxazoline)s as polymer therapeutics," Macromolecular Rapid Communications, 33(19):1613-1631 (2012).
Meyer et al., "Drug targeting using thermally responsive polymers and local hyperthermia," Journal of Controlled Release, 74(1-3):213-224 (2001).
PubChem Database, CID=32881 create date Mar. 27, 2005.
Rosa et al., "Poly(2-oxazoline)s: The versatile polymer platform for biomedicine," Material Matters, (2016).
Salgarella et al., Investigation of drug release modulation from poly(2-oxazoline) micelles through ultrasound, Scientific Reports, 8(1): 1-13 (2018).
Wiesbrock et al., "Microwave-Assisted Synthesis of a 42-Membered Library of Diblock Copoly(2-oxazoline)s and Chain-Extended Homo Poly(2-oxazoline)s and Their Thermal Characterization," Macromol. 38:7957-7966 (2005).
Wiesbrock et al., "Single-Mode Microwave Ovens as New Reaction Devices: Accelerating the Living Polymerization of 2-Ethyl-2-Oxazoline," Macromol. Rapid Commun. 25: 1895-1899 (2004).
Dargaville et al., "Poly(2-oxazoline) hydrogels: state-of-the-art and emerging applications," Macromolecular bioscience, 18(6):1800070 (2018).
Sahn et al., "LCST behavior of poly (2-ethyl-2-oxazoline) containing diblock and triblock copolymers," European Polymer Journal, 100:57-66 (2018).
Zhou et al., "Block length-dependent phase transition of poly (N-isopropylacrylamide)-b-poly (2-isoporpyl-2-oxazoline) diblock copolymer in water," Polymer, 153:250-261 (2018).
CAS Registry No. 26022-14-0 (Nov. 16, 1984).
International Preliminary Report on Patentability for International Application No. PCT/US2020/033730 dated Dec. 2, 2021.
Dworak et al., "Poly(2-substituted-2-oxazoline) surfaces for dermal fibroblasts adhesion and detachment" J Matter Sci: vol. 25, p. 1149-1163 (2014).
Fitjen et al., "Synthesis and Structure—Property relationships of random block copolymer: A direct comparison for coply(2-oxazoline)s" Macromolecules, vol. 40, 5879-5886 (2007).
Lambermont-Thijs et al., "Solubility Behavior of Amphiphilic Block and Random Copolymers Based on 2-Ethyl-2-oxazoline and 2-Nonyl oxazoline in Binary Water-Ethanol Mixtures" Journal of Polymer Science, vol. 47, p. 515-522 (2009).
Leiske et al., "How to tune the gene delivery and biocompatibility of poly(2-(4-aminobutyl)-2-oxazoline) by self- and coassembly" BioMacromolecules, vol. 19, p. 748-760 (2018).

* cited by examiner

COMPOSITIONS AND METHODS FOR CELLULAR DELIVERY

RELATED APPLICATIONS

This application is the U.S. National Stage of PCT/US2020/033730, filed May 20, 2020, which claims the benefit of U.S. Provisional Patent Application No. 62/850,514, filed on May 20, 2019. The contents of each of these applications are hereby incorporated by reference in their entirety.

GOVERNMENT SUPPORT

This invention was made with government support under Grant Number GM067555, awarded by the National Institutes of Health. The government has certain rights in the invention.

BACKGROUND

Hierarchical structure (e.g., micelle, vesicle, nanoparticle and nanoemulsion) formulations can improve the pharmaceutical properties of a biotherapeutic (e.g., a drug) by, for example, enhancing circulation half-life and facilitating the accumulation in a target tissue. Compared to conventional approaches, formulations of hierarchical structures can protect antigen/adjuvant payloads from the surrounding biological environment, thus increasing their half-life and minimizing their systemic toxicity. A critical advantage of the said formulations is the release of the payload at the desired site. Previously, approaches such as changes in pH or redox potential, the presence of an enzyme, or externally applied stimuli (light, heat, ultrasounds, magnetic field) are have been employed. However, to date, there are no formulations that respond to changes in macromolecule concentration, such as those that occur upon entry into a cell or other physical region where macromolecules are present at a higher concentration than in physiological fluids. Thus, there is an unmet need and accordingly, new formulations that respond to changes in macromolecule concentration are required.

SUMMARY OF THE INVENTION

In certain aspects, the present disclosure provides polymers comprising repeat units represented by formula Ia, formula Ib, formula Ic, formula Id, formula Ie, formula If, formula Ig, or formula Ih:

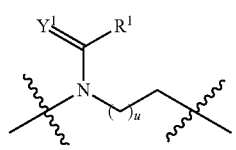

(Ia)

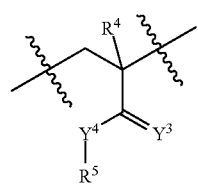

(Ib)

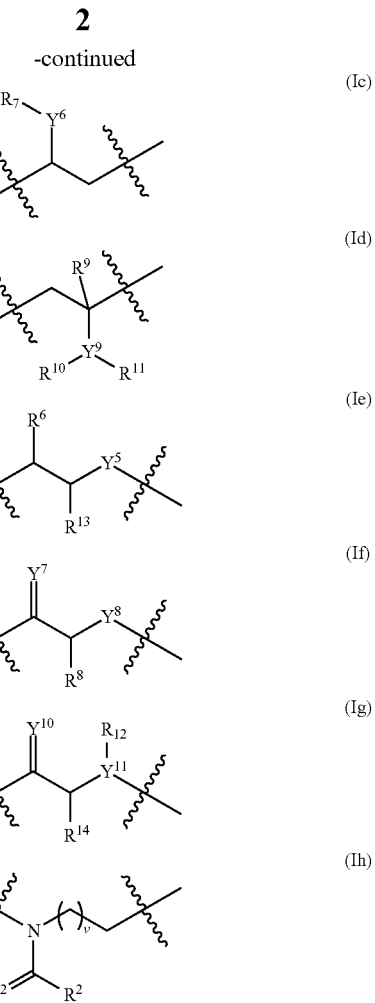

wherein:
R$^1$ is a group that imparts hydrophilic character to the polymer;
R$^2$ is a group that imparts hydrophobic character to the polymer;
Y$^1$, Y$^2$, Y$^3$, Y$^4$, Y$^5$, Y$^6$, Y$^7$, Y$^8$, Y$^9$, Y$^{10}$ and Y$^{11}$ are each independently selected from NR$^3$, O, or S, Se, P, C(R$^3$)$_2$
each R$^3$ is independently selected from hydrogen, alkyl, and aralkyl;
each R$^4$, R$^5$, R$^6$, R$^7$, R$^8$, R$^9$, R$^{10}$, R$^{11}$, R$^{12}$, and R$^{13}$ is independently selected from hydrogen, alkyl (e.g., perfluoroalkyl, perfluoroalkylalkyl, or heteroalkyl), cycloalkyl, arylalkyl, heteroaryl, and heterocyclyl;
hydrogen, alkyl, and aralkyl;
u is an integer from 1 to 10; and
v is an integer from 1 to 10.

In certain aspects, the present disclosure provides hierarchical structures comprising the polymers disclosed herein.

In certain aspects, the present disclosure provides pharmaceutical compositions comprising the polymers and/or hierarchical structures disclosed herein and at least one pharmaceutically acceptable excipient.

DETAILED DESCRIPTION OF THE INVENTION

Figure 1A:
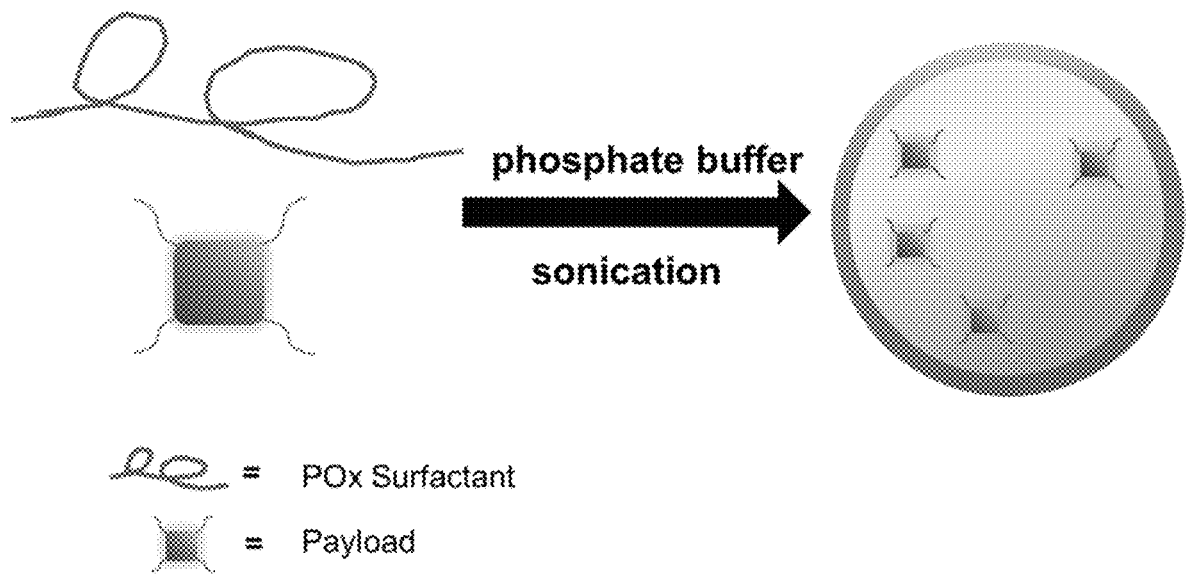
FIG. 1A depicts the formation of a hierarchical structure comprising poly(2-oxazoline) (POx) shell, an internal phase, and a payload (e.g., a bioactive agent).
Figure 1B:
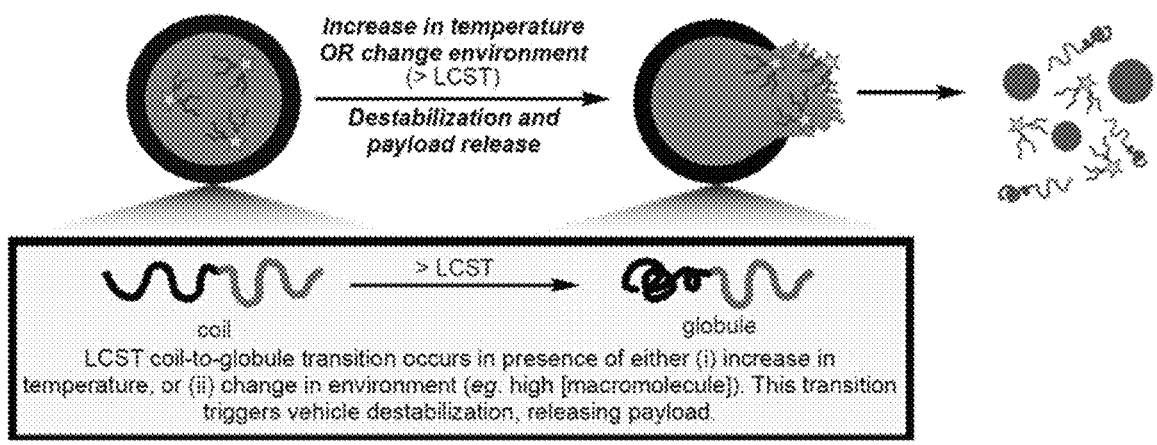
FIG. 1B depicts the response of a hierarchical structure (e.g., a POx nanoparticle) to environment changes, such as an increase in temperature. As the temperature increases, the hierarchical structure degrades, thereby releasing its payload (e.g., a bioactive agent).
Figure 1C:
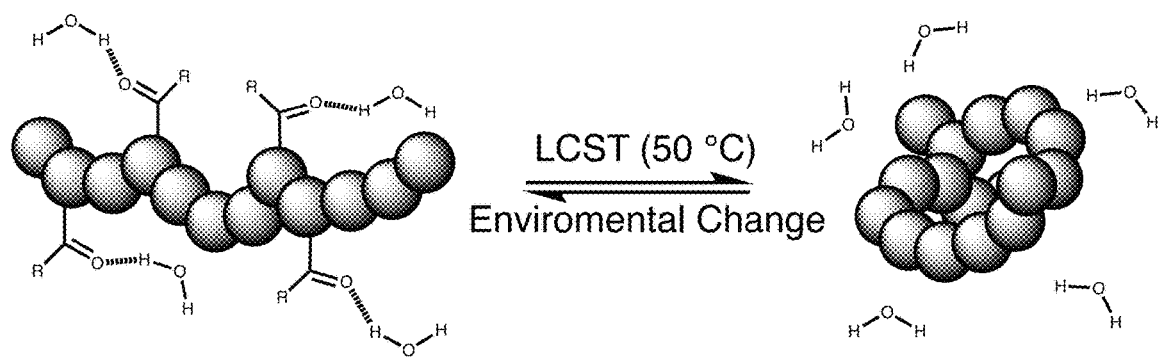
FIG. 1C depicts how polymer chains (e.g., POx polymer chains) change configuration in response to an increase or decrease in temperature.
Figure 1D:
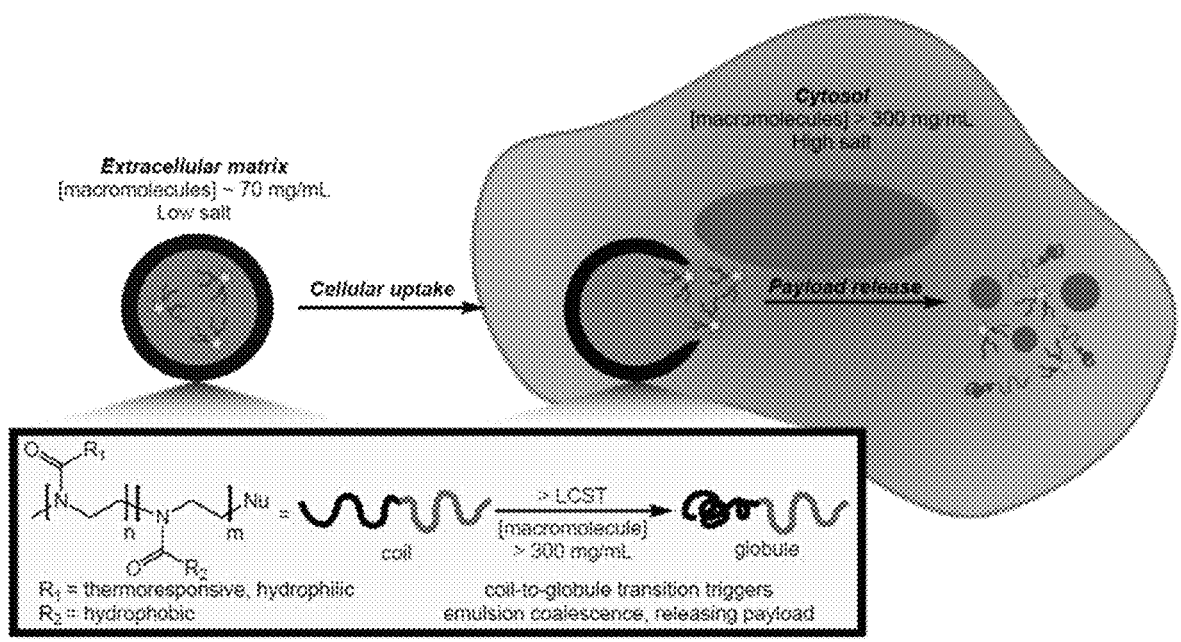
FIG. 1D depicts the internalization of a hierarchical structure (e.g., a POx nanoparticle) by a cell. When the hierarchical structure enters an environment containing a high concentration of salts, the hierarchical structure degrades, thereby releasing its payload (e.g., a bioactive agent).
Figure 2A:
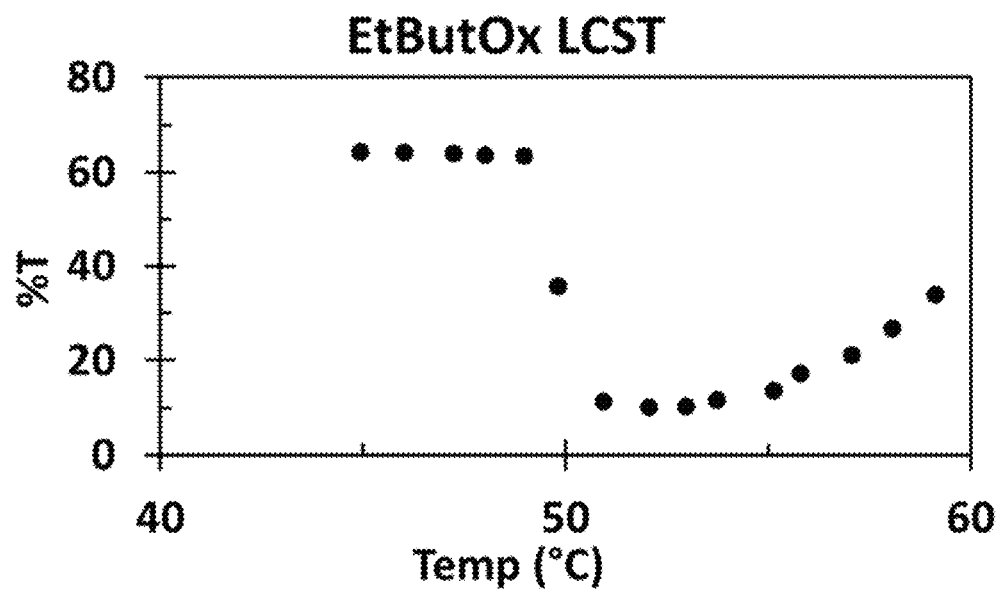
FIG. 2A shows the lower critical solution temperature (LCST) of a POx polymer. The LCST of the polymer is approximately 50° C.
Figure 2B:
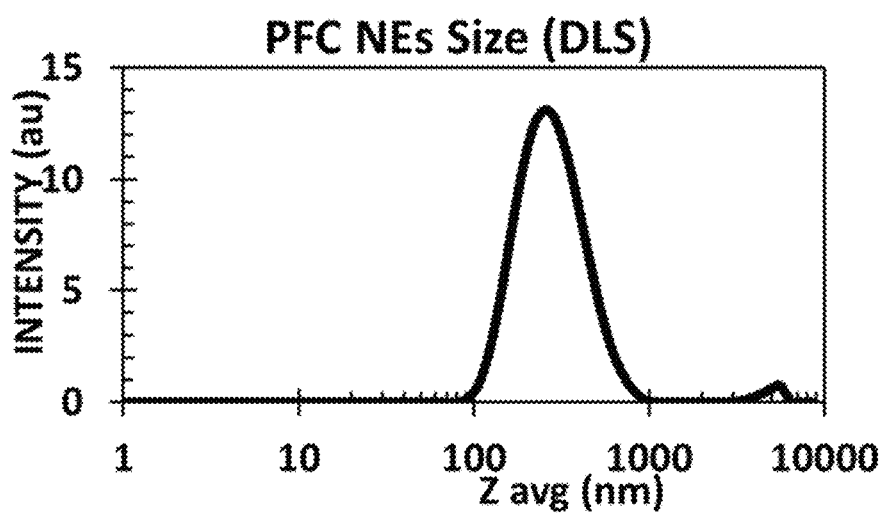
FIG. 2B shows the average size of hierarchical structures disclosed herein (e.g., POx nanoparticles). The average size of the hierarchical structure is approximately 200 nm.
Figure 2C:
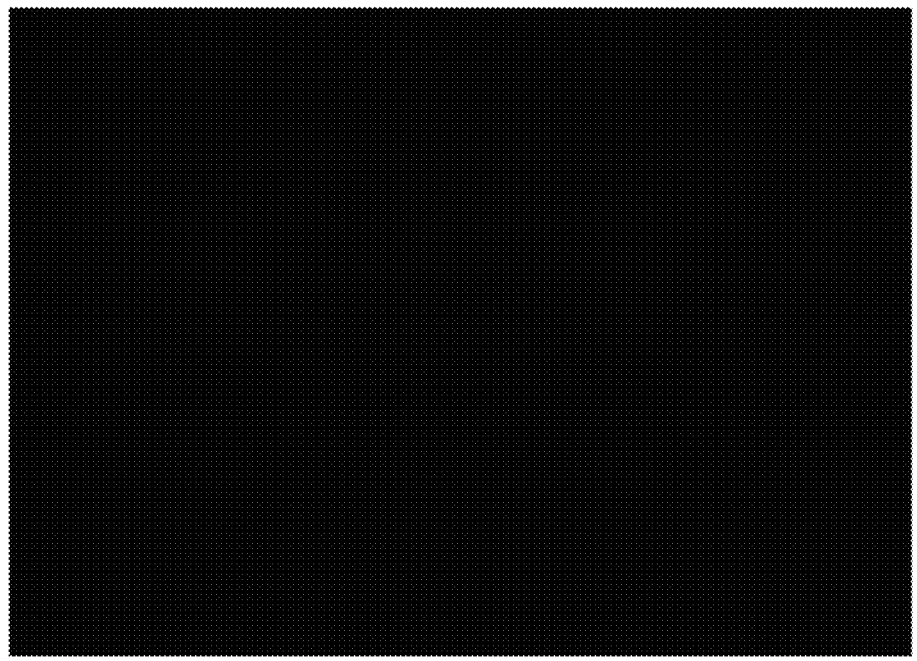
FIG. 2C shows the LCST of a $EtOx_{30}$-b-$ButOx_{10}$-t-OH hierarchical structure. The LCST of the polymer is approximately 55° C.
Figure 2D:
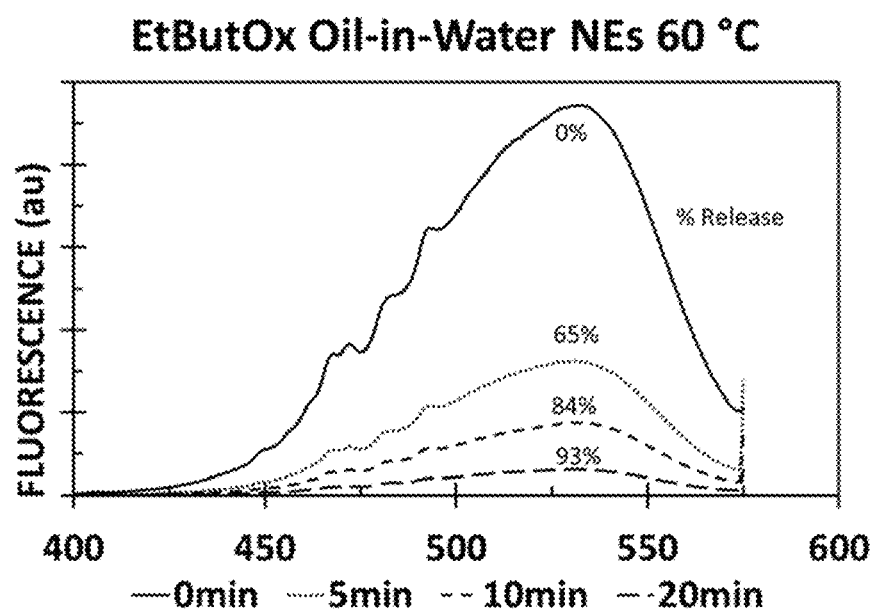
FIG. 2D shows the change in fluorescence as an $EtOx_{30}$-b-$ButOx_{10}$-t-OH hierarchical structure degrades and releases its payload. As the hierarchical structure degrades, the fluorescence decreases.
Figure 2E:
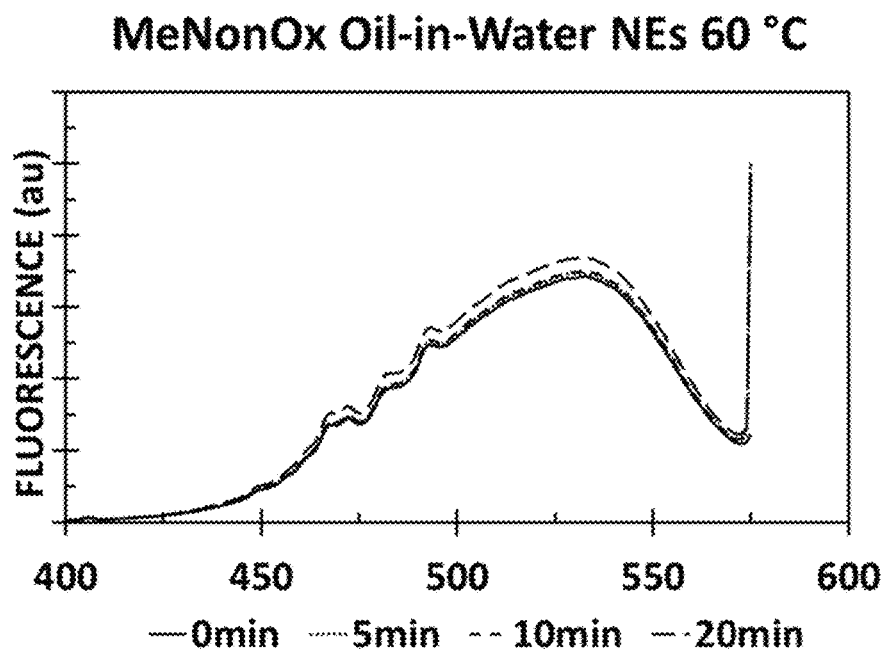
FIG. 2E shows minimal change in fluorescence as an $MeOx_{30}$-b-$NonOx_{10}$-t-OH (a surfactant lacking LCST) hierarchical structure does not degrade and does not release its payload following heating. Consequently, fluorescence does not decrease. This is a control for the experiment depicted in FIG. 2D
Figure 3:
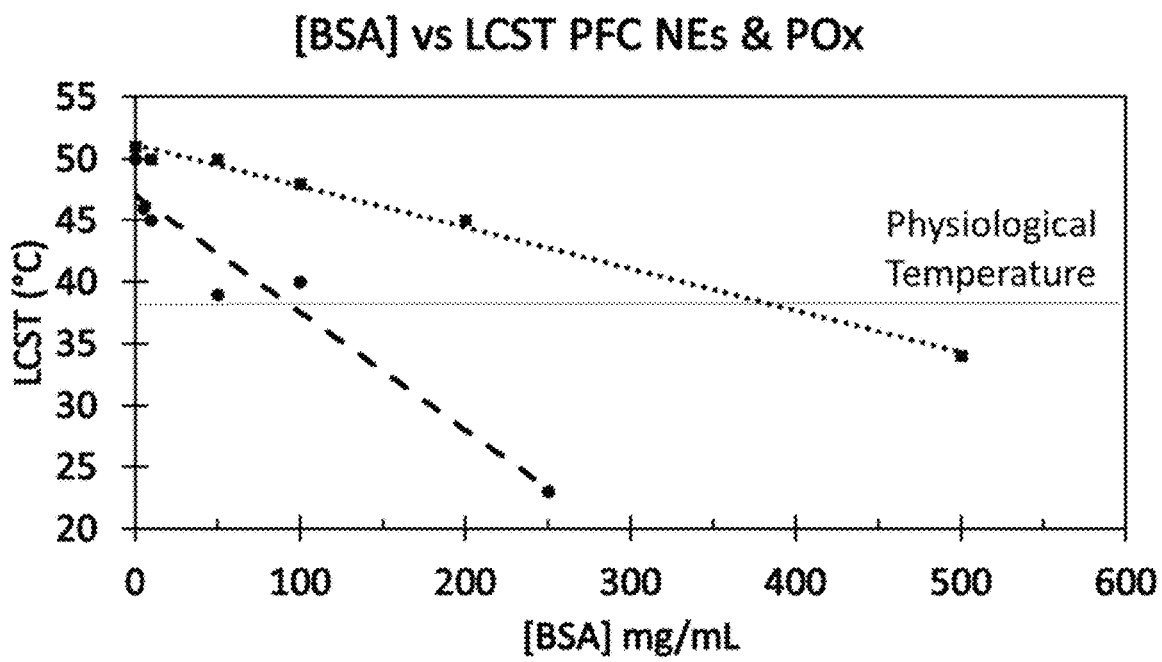
FIG. 3 shows the change in the LCST of both a POx hierarchical structure (e.g., a nanoemulsion) vs. a control polymer. As the concentration of BSA increase, the LCST of the hierarchical structure decreases.
Figure 4:
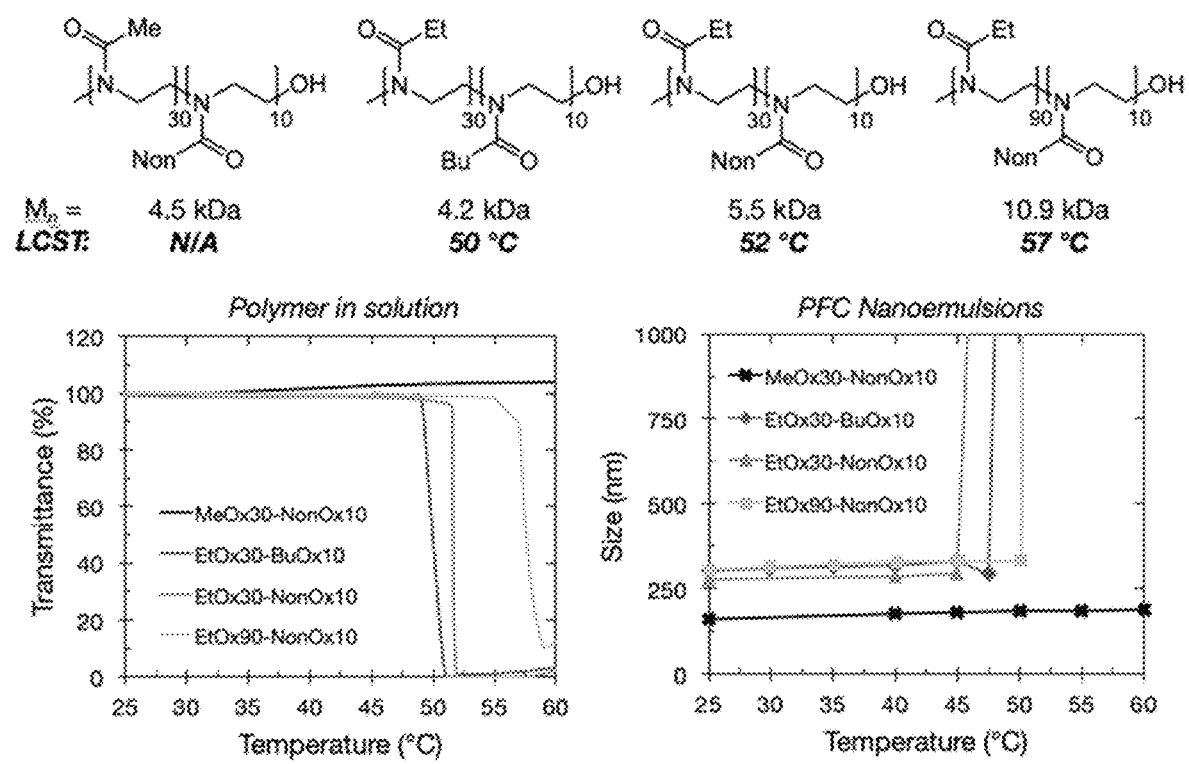
FIG. 4 shows the results of a panel of amphiphilic surfactants with varying hydrophilic and hydrophobic blocks, along with changes in block length. Me=—$CH_3$, Et=—$C_2H_5$, Bu=—$C_4H_9$, Non=—$C_9H_{19}$. Polymer in solution (micelles) LCST determined by measuring turbidity through a UV-vis spectrometer with temperature control, where a sudden increase in absorbance (or decrease in transmittance) accompanies the LCST transition. LCST-induced degradation of PFOB nanoemulsions was measured through DLS with temperature control, tracking size changes versus 5° C. temperature increments.
Figure 5:
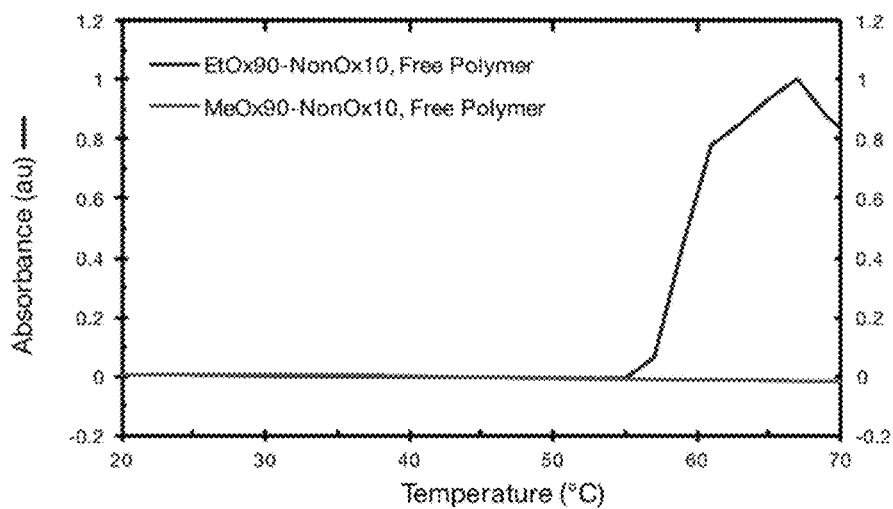
FIG. 5 shows the characterization of the LCST for polymeric micelles composed of either $P(EtOx)_{90}$-b-$P(NonOx)_{10}$ or $P(MeOx)_{90}$-b-$P(NonOx)_{10}$, dissolved in PBS at 5 mg/mL. Analyzed via UV-Vis spectrometry with temperature control at 2° C. increments.
Figure 6:
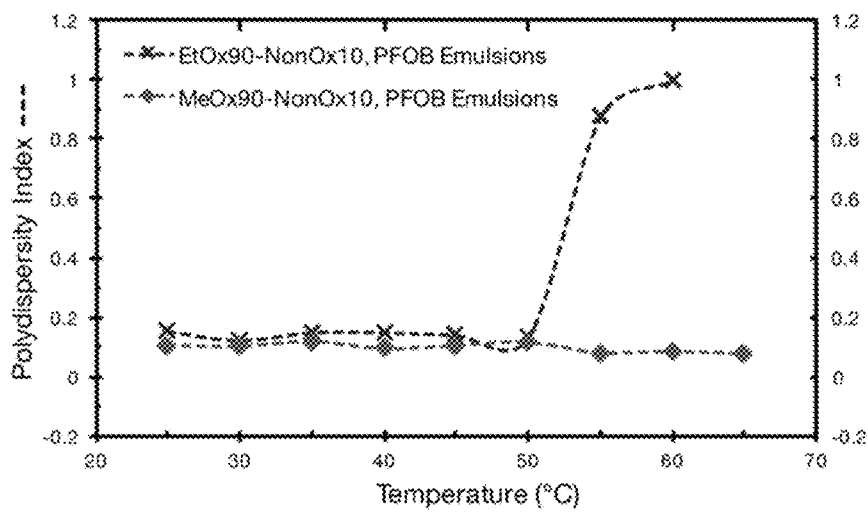
FIG. 6 shows the characterization of the LCST for perfluorooctylbromide nanoemulsions stabilized by either $P(EtOx)_{90}$-b-$P(NonOx)_{10}$ or $P(MeOx)_{90}$-b-$P(NonOx)_{10}$. Analyzed via Dynamic light scattering with temperature control at 5° C. increments.
Figure 7:
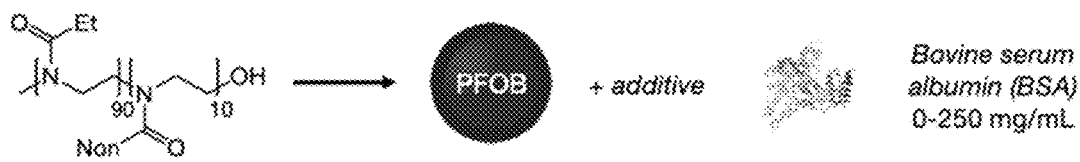
FIG. 7 shows the characterization of the LCST for perfluorooctylbromide nanoemulsions stabilized by $P(EtOx)_{90}$-b-$P(NonOx)_{10}$ in the presence of varying concentrations of BSA (0-250 mg/mL). For comparison to physiological fluids (e.g. blood), human serum (containing ~52 mg/mL of human serum albumin) and fetal bovine serum (containing ~36 mg/mL of bovine serum albumin) are included. When the hydrophilic block is altered to $P(MeOx)_{90}$, there is still no observable LCST up to 65° C., even in the presence of BSA (100 mg/mL).
Figure 7:
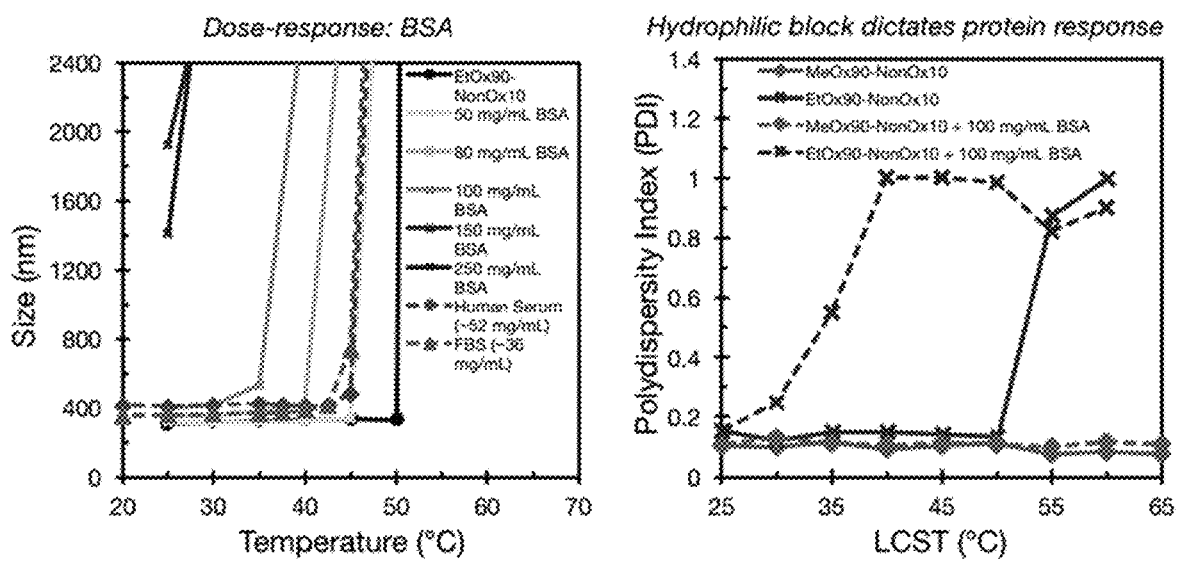
Figure 8:
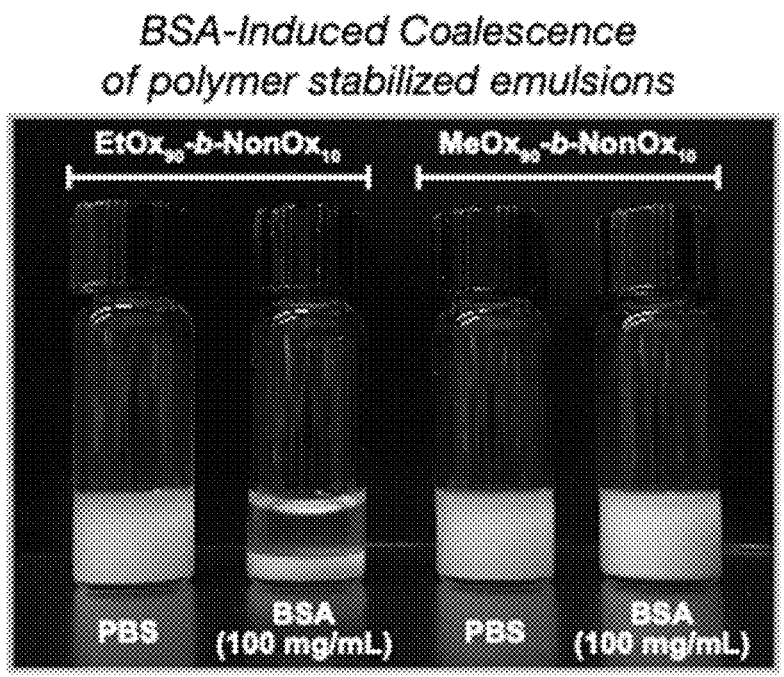
FIG. 8 shows that phase separation is observed for nanoemulsions only when (i) stabilized by $P(EtOx)_{90}$-b-$P(NonOx)_{10}$, (ii) in the presence of BSA (100 mg/mL), and (iii) heated to 37° C. Lower layer=perfluorooctylbromide, upper layer=PBS+BSA.
Figure 9:
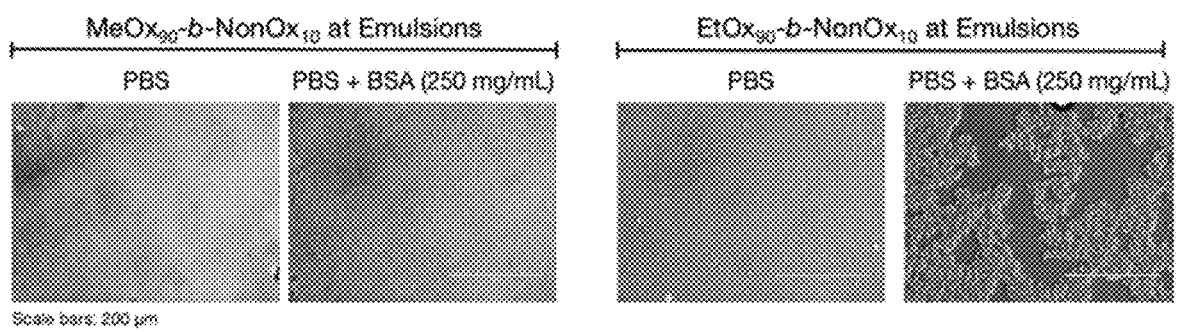
FIG. 9 shows that microscopic phase separation at increased concentrations of BSA in PBS (250 mg/mL) is observed PFOB nanoemulsions stabilized by polymeric surfactant were injected directly into a PBS+/−BSA solution and directly imaged using an epifluorescence microscope (scale bars: 200 μM).
Figure 10:
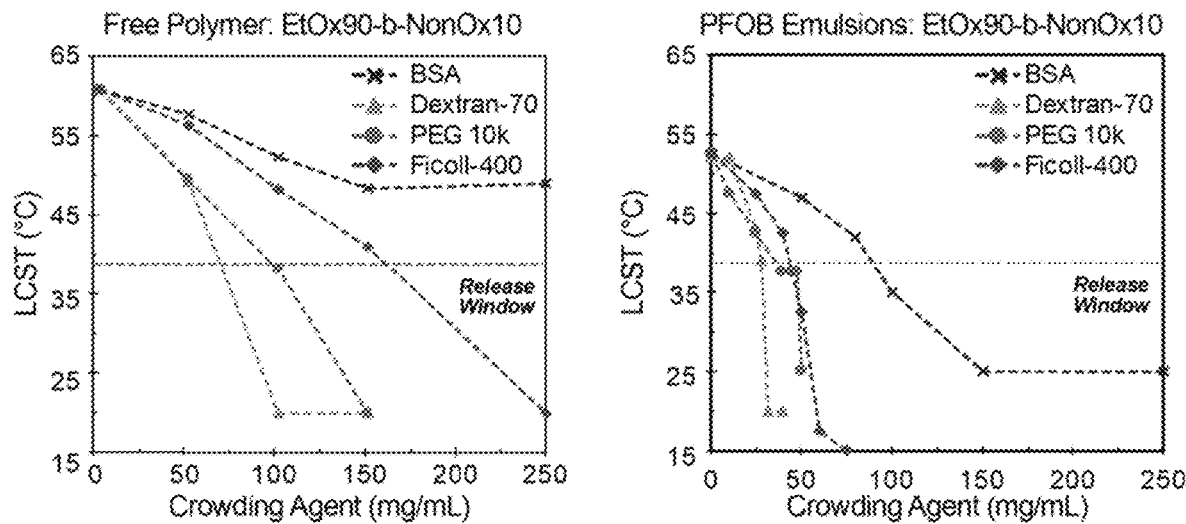
FIG. 10 is a plot of the LCST (° C.) versus crowding agent (mg/mL) for both (i) free polymer $P(EtOx)_{90}$-b-$P(NonOx)_{10}$ in solution (i.e. hierarchical structure=micelles) and (ii) PFOB emulsions stabilized by $P(EtOx)_{90}$-b-$P(NonOx)_{10}$. "Release window" is determined as temperature below that of physiological temperature (37° C.) and above the crowding expected in a physiological fluid (~80 mg/mL).
Figure 11:
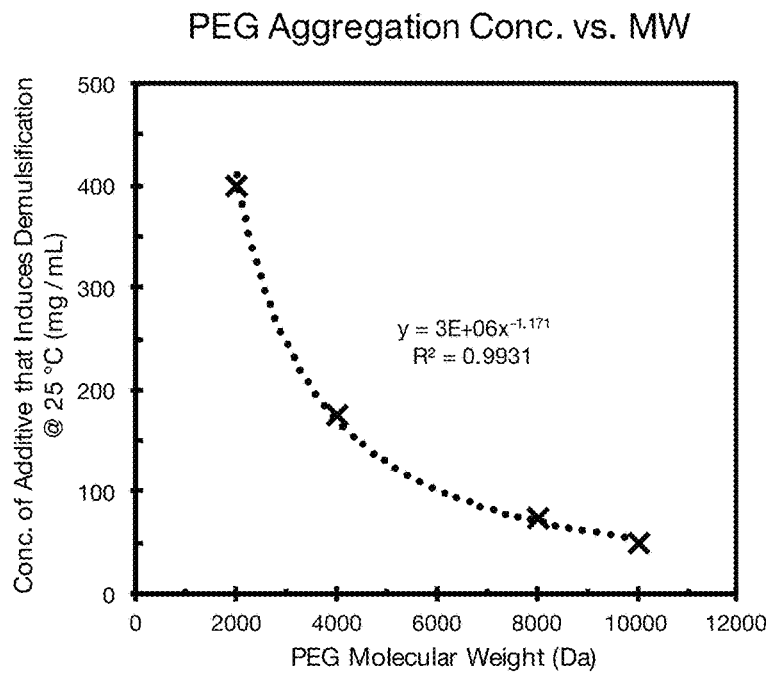
FIG. 11 is a plot of aggregation concentration (mg/mL) versus molecular weight for a series of poly(ethylene glycol) (PEG) additives. Aggregation concentration is defined as the minimum concentration of PEG that is needed to induce demulsification of $P(EtOx)_{90}$-b-$P(NonOx)_{10}$ stabilized PFOB nanoemulsions at room temperature (25° C.).
Figure 12:
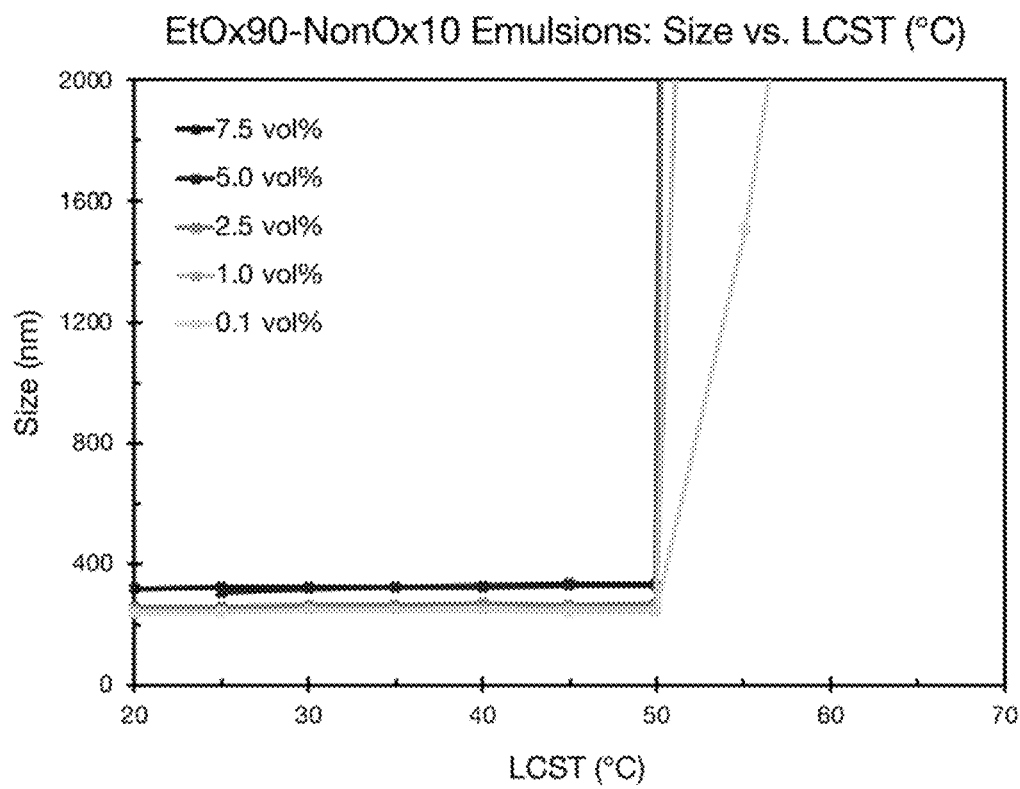
FIG. 12 shows the results of serial dilutions of $P(EtOx)_{90}$-b-$P(NonOx)_{10}$-stabilized PFOB emulsions in PBS (pH 7.4). Droplet diameters (nm) were tracked versus temperature (° C.) for each diluted solution, from 20 to 70° C., using dynamic light scattering.
Figure 13:
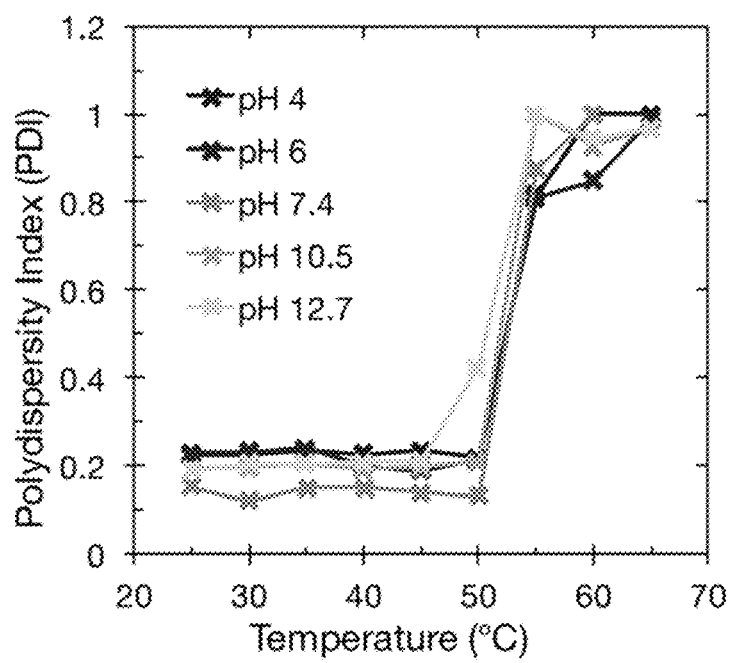
FIG. 13 shows the dependence of LCST on pH for $P(EtOx)_{90}$-b-$P(NonOx)_{10}$-stabilized PFOB emulsions in PBS. Solutions were pH' d using 0.5 mM NaOH or HCl.
Figure 14:
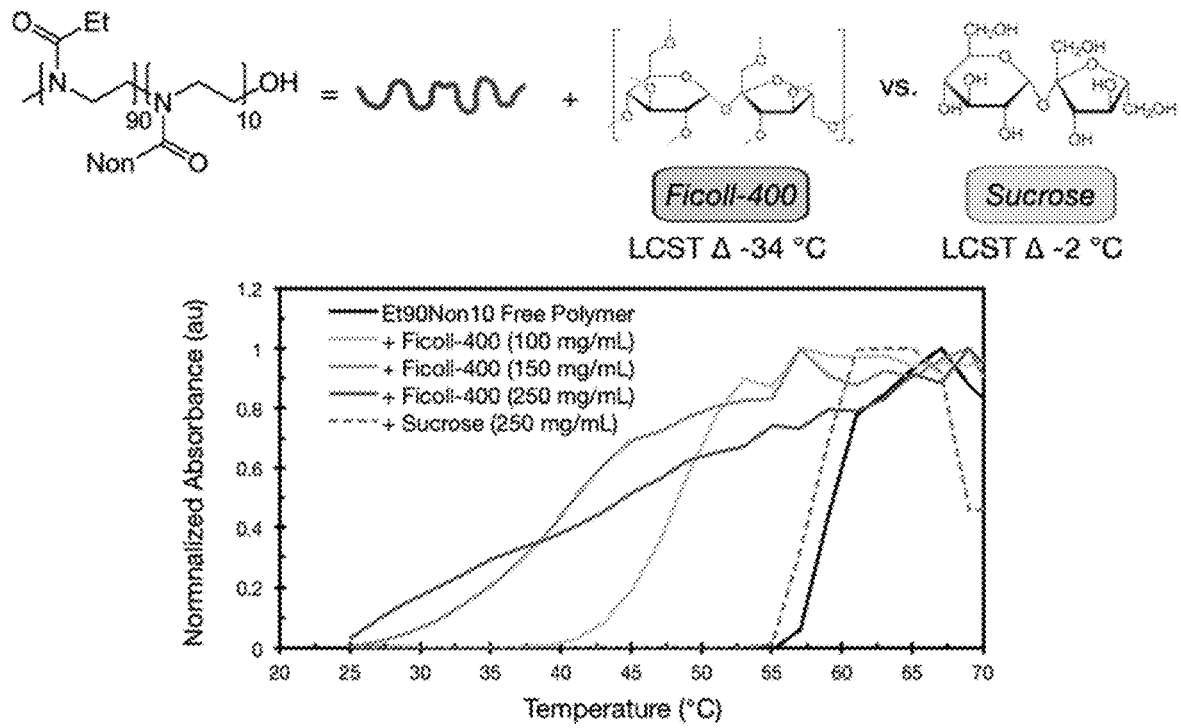
FIG. 14 is a plot of normalized absorbance (au) traces versus temperature (° C.) for micellar $P(EtOx)_{90}$-b-$P(NonOx)_{10}$ in the presence of either macromolecular crowding agent Ficoll-400 (0-250 mg/mL) or control monomer sucrose (250 mg/mL). Compared to equal concentrations of Ficoll-400 crowder, monomeric sucrose has a negligible influence on the LCST, showing the significance of macromolecular crowding.
Figure 15:
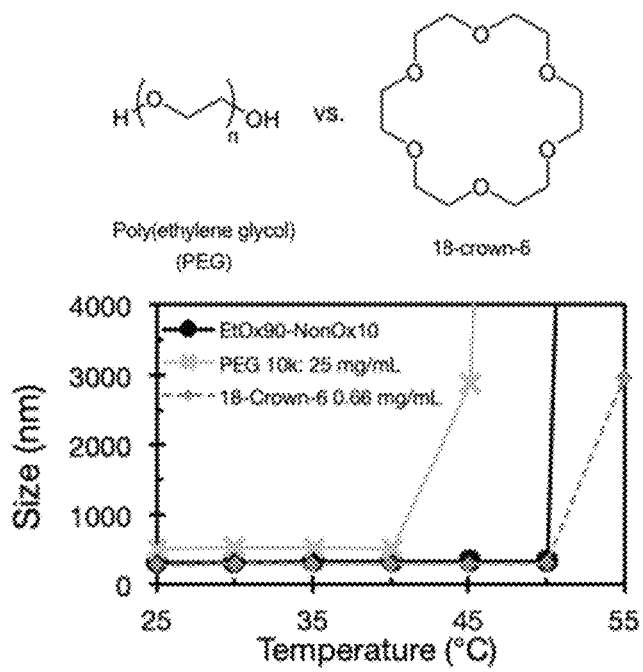
FIG. 15 is a plot of size (nm) versus temperature (° C.) for $P(EtOx)_{90}$-b-$P(NonOx)_{10}$ stabilized PFOB nanoemulsions in the presence of either macromolecular crowding agent PEG-10k (25.0 mg/mL) or equimolar 18-crown-6 (0.7 mg/mL), capable of making the same number of hydrogen bonds to neighboring water molecules. Compared to equimolar PEG-10k, 18-crown-6 additive has a negligible influence on emulsion degradation temperature, indicating that the mechanism of LCST reduction is not competition for hydration water.
Figure 16:
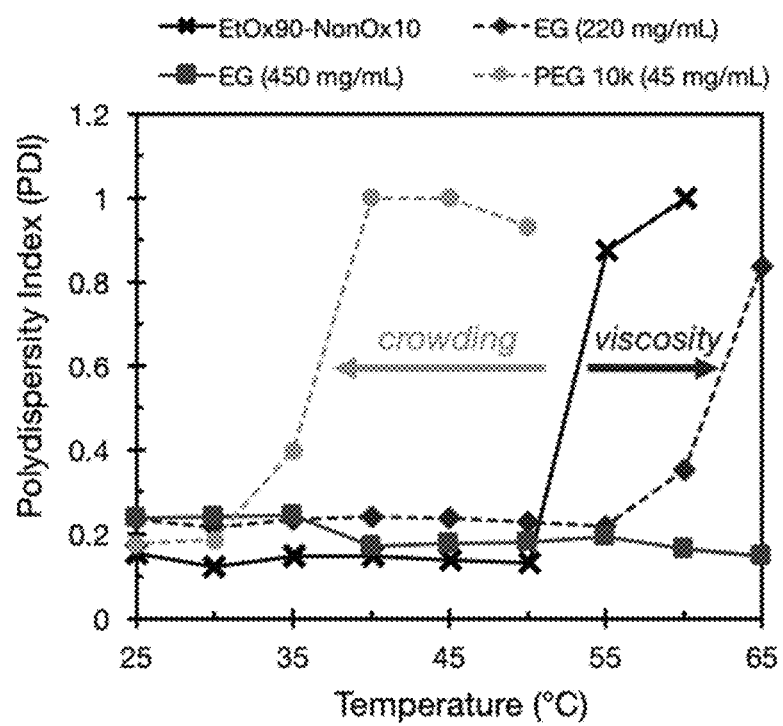
FIG. 16 is a plot of polydispersity index (PDI) versus temperature (° C.) for $P(EtOx)_{90}$-b-$P(NonOx)_{10}$ stabilized PFOB nanoemulsions in the presence of either macromolecular crowding agent PEG-10k, or small molecule viscogen ethylene glycol (EG). Compared to an equally viscous solution composed of PEG-10k, a viscous solution of EG increases the LCST, showing that the decrease in LCST is not attributable to changes in viscosity.

The lower critical solubility temperature (LCST) of a polymer denotes the temperature at which a polymer under-goes a random coil-to-globule transition. In aqueous media, below this temperature polymers remain soluble; above this temperature, polymers transition to an insoluble, globular state. The LCST can be affected by both intrinsic and extrinsic factors which influence entropic or enthalpic effects including, but not limited to, solvent, polymer hydrophilic-lipophilic balance (HLB), and additives (e.g. salt or macromolecules).

Amphiphilic polymers, such as poly(2-oxazoline)s (POx), are a class of biocompatible surfactants that possess a wide range of chemistries, such as tunable lower critical solution temperature (LCST) and the ability to form self-assembled nanostructures and stabilize nanoemulsions (NEs). Furthermore, the LCST of a hierarchical structure formed from certain polymers (e.g., POx) may be altered in response to certain environmental changes, such as pH, salt concentration, and/or macromolecule concentration.

The LCST of hierarchical structures formed from certain polymers, such as poly(2-oxazoline)s, poloxamers, acrylates, methacrylates, or polyamides, may be exploited to induce aggregation at high concentrations of macromolecules, such as those found inside the cell. Polymers can be designed such that at low concentrations (e.g. <50 mg/mL) of protein, the LCST remains below physiological temperature (37° C.). However, at high concentrations (e.g. >250 mg/mL) of protein, the LCST is reduced below 37° C., and the poly(2-oxazoline) amphiphiles aggregate. As the concentration of macromolecules in cellulo is orders of magnitude higher than in extracellular matrices (a phenomenon known as the macromolecular crowding effect), this change in macromolecular crowding can be used as a trigger to affect polymeric assemblies in cellulo.

Higher-order stimuli-responsive hierarchical structures (e.g., micelles, vesicles, nanoparticles, or nanoemulsions) may be constructed to exploit these phenomena. When soluble, poly(2-oxazoline) amphiphiles disclosed herein act as effective surfactants for forming such structures, and stability is imparted by unfavorable polymer-polymer mixing interactions between polymer-coated emulsions, causing emulsion-emulsion repulsion. However, upon an LCST transition, polymer-polymer mixing is favorable, which causes de-emulsification. This may occur, for example, via a coalescence mechanism. Such emulsions degrade rapidly in high concentrations of macromolecules (e.g. >250 mg/mL).

Accordingly, the hierarchical structures disclosed herein respond to physiologically relevant stimulus and have many applications, for instance as delivery systems in the cosmetic, food, and pharmaceutical industries.

In one aspect, the present disclosure provides polymers comprising repeat units represented by formula Ia, formula Ib, formula Ic, formula Id, formula Ie, formula If, formula Ig, or formula Ih:

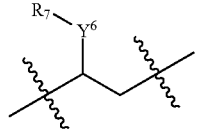
(Ia)

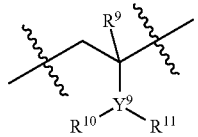
(Ib)

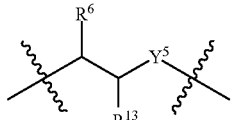
(Ic)

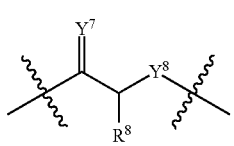
(Id)

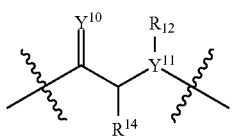
(Ie)

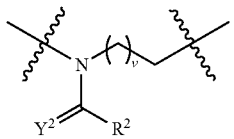
(If)

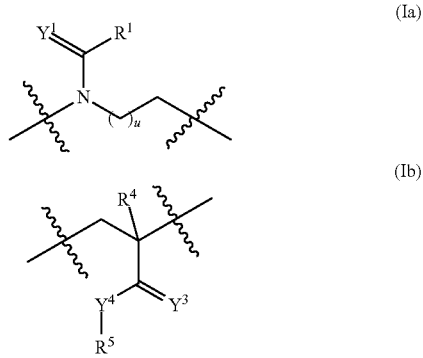
(Ig)

(Ih)

wherein:
$R^1$ is a group that imparts hydrophilic character to the polymer;
$R^2$ is a group that imparts hydrophobic character to the polymer;
$Y^1$, $Y^2$, $Y^3$, $Y^4$, $Y^5$, $Y^6$, $Y^7$, $Y^8$, $Y^9$, $Y^{10}$ and $Y^{11}$ are each independently selected from $NR^3$, O, or S, Se, P, $C(R^3)_2$
each $R^3$ is independently selected from hydrogen, alkyl, and aralkyl;
each $R^4$, $R^5$, $R^6$, $R^7$, $R^8$, $R^9$, $R^{10}$, $R^{11}$, $R^{12}$, and $R^{13}$ is independently selected from hydrogen, alkyl (e.g., perfluoroalkyl, perfluoroalkylalkyl, or heteroalkyl), cycloalkyl, arylalkyl, heteroaryl, and heterocyclyl;
hydrogen, alkyl, and aralkyl;
u is an integer from 1 to 10; and
v is an integer from 1 to 10.

Typically, the polymers disclosed herein comprise repeat units (e.g., monomers) in a range of configurations. For example, the polymer may contain only one type of repeat units. Alternatively, the polymer may contain more than one type of repeat unit (e.g., 2, 3, 4, or 5 types of repeat units). When the polymer contains more than one type of repeat unit, the repeat units may be arranged in contiguous blocks (e.g., -A-A-A-A-B-B-B-B-), alternating blocks (e.g., -A-A-A-A-B-B-B-A-A-A-A-) or the arrangement of the repeat units may be random (e.g., -A-B-B-A-B-A-A-). In certain embodiments, the polymers disclosed herein comprise from 1 to 500 repeat units.

In certain embodiments, the polymer comprises repeat units represented by formula Ia or formula Ih:

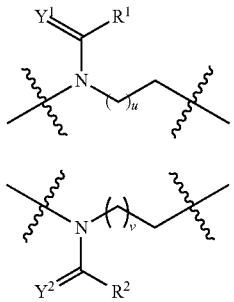
(Ia)

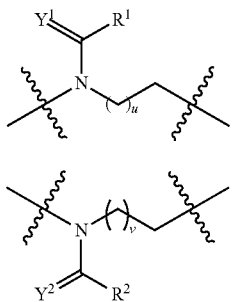
(Ih)

wherein:
R$^1$ is a group that imparts hydrophilic character to the polymer;
R$^2$ is a group that imparts hydrophobic character to the polymer;
Y$^1$ and Y$^2$ are independently selected from NR$^3$, O, or S;
each R$^3$ is independently selected from hydrogen, alkyl, and aralkyl;
u is an integer from 1 to 10; and
v is an integer from 1 to 10.

In certain embodiments, the polymer comprises repeat units represented by formula Ia and formula Ih:

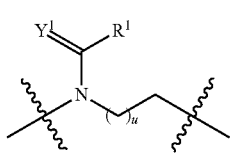
(Ia)

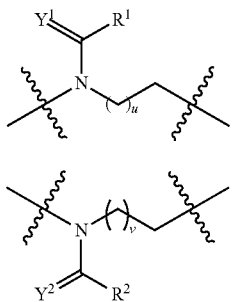
(Ih)

wherein:
R$^1$ is a group that imparts hydrophilic character to the polymer;
R$^2$ is a group that imparts hydrophobic character to the polymer;
Y$^1$ and Y$^2$ are independently selected from NR$^3$, O, or S;
each R$^3$ is independently selected from hydrogen, alkyl, and aralkyl;
u is an integer from 1 to 10; and
v is an integer from 1 to 10.

In certain embodiments, the polymer consists essentially of repeat units represented by formula Ia and formula Ih:

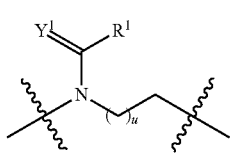
(Ia)

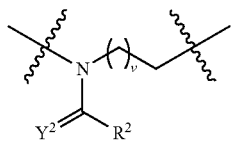
(Ih)

wherein:
R$^1$ is a group that imparts hydrophilic character to the polymer;
R$^2$ is a group that imparts hydrophobic character to the polymer;
Y$^1$ and Y$^2$ are independently selected from NR$^3$, O, or S;
each R$^3$ is independently selected from hydrogen, alkyl, and aralkyl;
u is an integer from 1 to 10; and
v is an integer from 1 to 10.

In certain embodiments, the polymer is represented by formula Ia or formula Ih:

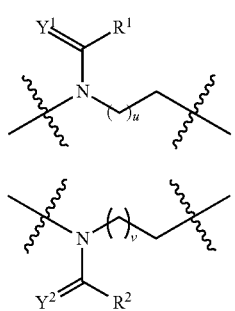
(Ia)

(Ih)

wherein:
R$^1$ is a group that imparts hydrophilic character to the polymer;
R$^2$ is a group that imparts hydrophobic character to the polymer;
Y$^1$ and Y$^2$ are independently selected from NR$^3$, O, or S;
each R$^3$ is independently selected from hydrogen, alkyl, and aralkyl;
u is an integer from 1 to 10; and
v is an integer from 1 to 10.

In certain embodiments, the polymer comprises a block W and a block X wherein:
block W comprises at least one repeat unit of formula Ib, formula Ic, formula Id, formula Ie, formula If, or formula Ig; and
block X comprises at least one repeat unit of formula Ih.

In certain embodiments, the polymer consists essentially of a block W and a block X wherein:
block W comprises at least one repeat unit of formula Ib, formula Ic, formula Id, formula Ie, or formula If, formula Ig; and
block X comprises at least one repeat unit of formula Ih.

In certain embodiments, the polymer consists essentially of a block W and a block X wherein:
block W consists essentially of at least one repeat unit of formula Ib, formula Ic, formula Id, formula Ie, or formula If, formula Ig; and
block X comprises at least one repeat unit of formula Ih.

In certain embodiments, the polymer consists essentially of a block W and a block X wherein:

block W consists essentially of at least one repeat unit of formula Ib, formula Ic, formula Id, formula Ie, or formula If, formula Ig; and block X consists essentially of at least one repeat unit of formula Ih.

In certain embodiments, the polymer consists essentially of a block W and a block X wherein:

block W consists essentially of at least one repeat unit of formula Ib; and block X consists essentially of at least one repeat unit of formula Ih.

In certain embodiments, the polymer consists essentially of a block W and a block X wherein:

block W consists essentially of at least one repeat unit of formula Ic; and block X consists essentially of at least one repeat unit of formula Ih. In certain embodiments, the polymer consists essentially of a block W and a block X wherein:

block W consists essentially of at least one repeat unit of formula Id; and block X consists essentially of at least one repeat unit of formula Ih.

In certain embodiments, the polymer consists essentially of a block W and a block X wherein:

block W consists essentially of at least one repeat unit of formula Ie; and block X consists essentially of at least one repeat unit of formula Ih.

In certain embodiments, the polymer consists essentially of a block W and a block X wherein:

block W consists essentially of at least one repeat unit of formula If; and block X consists essentially of at least one repeat unit of formula Ih.

In certain embodiments, the polymer consists essentially of a block W and a block X wherein:

block W consists essentially of at least one repeat unit of formula Ig; and block X consists essentially of at least one repeat unit of formula Ih.

In certain embodiments, the polymer comprises a block W and a block X wherein:

block W comprises at least one repeat unit of formula Ia; and block X comprises at least one repeat unit of formula Ih.

In certain embodiments, the polymer consists essentially of a block W and a block X wherein:

block W comprises at least one repeat unit of formula Ia; and block X comprises at least one repeat unit of formula Ih.

In certain embodiments, the polymer consists essentially of a block W and a block X wherein:

block W consists essentially of at least one repeat unit of formula Ia; and block X comprises at least one repeat unit of formula Ih.

In certain embodiments, the polymer consists essentially of a block W and a block X wherein:

block W consists essentially of at least one repeat unit of formula Ia; and block X consists essentially at least one repeat unit of formula Ib.

In certain embodiments, block W comprises from 1 to 500 repeat units, preferably 90 repeat units. In certain preferred embodiments, block W comprises 30 repeat units. In other preferred embodiments, block W comprises 90 repeat units.

In certain embodiments, block X comprises from 1 to 50 repeat units, preferably 10 repeat units.

In certain embodiments, the polymer contains more than one block of W.

In certain embodiments, the polymer contains more than one block of X.

In certain embodiments, the ratio of blocks W:X is from about 1:1 to about 20:1. In certain embodiments, the ratio of blocks W:X is from about 1:1 to about 5:1. In certain preferred embodiments, the ratio of blocks W:X is about 3:1. In other preferred embodiments, the ratio of blocks W:X is about 9:1. In certain embodiments, the ratio of blocks X:W is about 1:1 to about 5:1.

In certain embodiments, the polymer contains one block of W and one block of X.

In certain preferred embodiments, block W contains 30 repeat units and block X contains 10 repeat units. In other preferred embodiments, block W contains 90 repeat units and block X contains 10 repeat units.

In certain preferred embodiments, block W contains about 30 repeat units and block X contains about 10 repeat units. In other preferred embodiments, block W contains about 90 repeat units and block X contains about 10 repeat units.

In certain embodiments, the ratio of repeat units comprising a hydrophilic group to repeat units comprising a hydrophobic group is from about 2:1 to about 20:1. In certain preferred embodiments, the ratio of repeat units comprising a hydrophilic group to repeat units comprising a hydrophobic group is about 3:1. In certain other preferred embodiments, the ratio of repeat units comprising a hydrophilic group to repeat units comprising a hydrophobic group is about 9:1.

In certain embodiments, the polymer is represented by formula II:

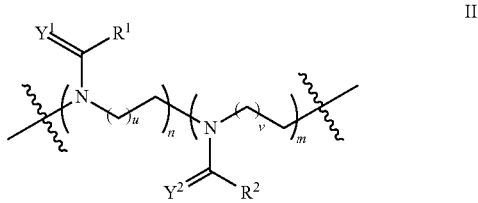

wherein:

n is an integer from 1 to 500; and m is an integer from 1 to 500.

In certain preferred embodiments of formula II, n is about 30. In other preferred embodiments, n is about 90.

In certain preferred embodiments of formula II, m is about 10.

In certain preferred embodiments of formula II, the ratio of n:m is about 9:1. In other preferred embodiments, the ratio of n:m is about 3:1

In certain embodiments, the polymer further comprises an end group L selected from a nucleophile, a biomolecule, or a polymer chain (e.g., polyethylene glycol chain).

In certain embodiments, the polymer is represented by formula III:

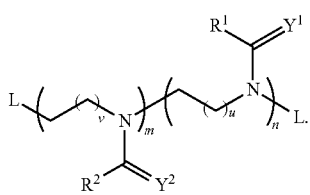

III

In certain embodiments of formulas I, II, and III, $Y^1$ is oxygen.

In certain embodiments of formulas I, II, and III, $Y^2$ is oxygen.

In certain embodiments of formulas I, II, and III, $R^1$ is $C_1$-$C_3$ alkyl. In certain preferred embodiments, $R^1$ is alkenyl (e.g., vinyl or allyl). In other preferred embodiments, $R^1$ is sulfonylalkyl. In yet other preferred embodiments, $R^1$ is hydroxyalkyl.

In certain embodiments of formulas I, II, and III, $R^2$ is $C_3$-$C_{20}$alkyl. In certain preferred embodiments, $R^2$ is n-propyl, butyl, octyl, or nonyl. In other preferred embodiments, $C_4$-$C_{20}$fluoroalkyl (e.g., $C_4$-$C_{20}$perfluoroalkyl or $C_4$-$C_{20}$perfluoroalkylalkyl). In certain even further preferred embodiments, $R^2$ is tridecafluorooctanyl. In other embodiments, $R^2$ is cycloalkyl. In other embodiments, $R^2$ is aryl.

In certain embodiments of formulas I, II, and III, u is 1.

In certain embodiments of formulas I, II, and III, v is 1.

In certain embodiments, the polymer further comprises a block Z and Z is a repeat unit represented by formula IV:

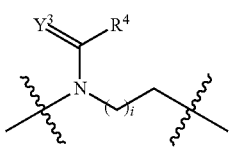

IV wherein:
$Y^3$ selected from $NR^3$, O, or S;
$R^4$ is a linking moiety (e.g., a precursor to a click reaction); and
i is an integer from 1 to 10.

In certain embodiments, the linking moiety is capable of participating in a 1,3-dipolar cycloaddition reaction, a hetero-diels reaction, a nucleophilic substitution reaction, a non-aldol type carbonyl reaction, an oxidation reaction, or a click reaction. In certain preferred embodiments, the linking moiety is capable of participating in a click reaction. In certain embodiments, the linking moiety is an azide, an alkene, or an alkyne.

In certain embodiments of formula IV, $R^4$ is alkenyl (e.g., butenyl). In other embodiments, $R^4$ is alkynyl (e.g., ethynyl).

In certain embodiments of formula IV, $Y^3$ is oxygen.

In certain embodiments, of formula IV, i is 1.

In certain preferred embodiments of formula IV, Z comprises from 1 to 30 repeat units. In other preferred embodiments, Z comprises from 1 to 90 repeat units.

In certain embodiments, the polymer contains one block of Z. In other embodiments, the polymer contains more than one block of Z.

In certain embodiments of formulas II and III, L is a biomolecule (e.g., a protein). In certain embodiments, L is a nucleophile. In certain embodiments, L is amino, hydroxyl, carboxyl, amido, thio, sulfonyl, or sulfoxyl.

In certain preferred embodiments, the polymer is capable of forming hierarchical structures.

In another aspect, the present disclosure provides a plurality of polymers of the disclosure.

In certain embodiments, the plurality of polymers has a number average of repeat units in W from 1 to 500. In certain preferred embodiments, the plurality of polymers has a number average of repeat units in W of about 30. In other preferred embodiments, the plurality of polymers has a number average of repeat units in W of about 90.

In certain embodiments, the plurality of polymers has a polydispersity of between 1-1.5. In certain embodiments, the plurality of polymers has a polydispersity of between 1-1.4. In certain preferred embodiments, the plurality of polymers has a polydispersity of between 1-1.3. In certain preferred embodiments, the plurality of polymers has a polydispersity of about 1, about 1.1, about 1.2, about 1.3, about 1.4, or about 1.5. In certain preferred embodiments, the plurality of polymers has a polydispersity of about 1.3.

In certain embodiments, the plurality of polymers has a number average of repeat units in X from 1 to 50. In certain preferred embodiments, the plurality of polymers has a number average of repeat units in X of about 10.

In certain preferred embodiments, the plurality of polymers has a number average of repeat units in W of about 30 and a number average of repeat units in X of about 10. In certain embodiments, the plurality of polymers has a number average molecular weight of between 4,000 to 6,000. In certain embodiments, the plurality of polymers has a number average molecular weight of between 4,500 to 5,500. In preferred certain embodiments, the plurality of polymers has a number average molecular weight of between 4,800 to 5,200. In certain embodiments, the plurality of polymers has a number average molecular weight of about 4,000, about 4,200, about 4,400, about 4,600, about 4,800, about 5,000, about 5,200, about 5,400, about 5,600, about 5,800, or about 6,000. In certain preferred embodiments, the plurality of polymers has a number average molecular weight of about 4,600, about 4,800, about 5,000, about 5,200, or about 5,400. In certain even further preferred embodiments, the plurality of polymers has a number average molecular weight of about 4,800, about 5,000, or about 5,200. In certain even further preferred embodiments, the plurality of polymers has a number average molecular weight of about 4,900. In certain embodiments, the plurality of polymers has a weight average molecular weight of between 5,000 to 8,000. In certain embodiments, the plurality of polymers has a weight average molecular weight of between 5,500 to 7,500. In certain preferred embodiments, the plurality of polymers has a weight average molecular weight of between 6,000 to 7,000. In certain preferred embodiments, the plurality of polymers has a weight average molecular weight of between 6,200 to 6,800. In certain embodiments, the plurality of polymers has a weight average molecular weight of about 5,000, about 5,200, about 5,400, about 5,600, about 5,800, about 6,000, about 6,200, about 6,400, about 6,600, about 6,800, about 7,000, about 7,200, about 7,400, about 7,600, about 7,800, or about 8,000. In certain embodiments, the plurality of polymers has a weight average molecular weight of about 5,800, about 6,000, about 6,200, about 6,400, about 6,600, about 6,800, about 7,000, or about 7,200. In certain preferred embodiments, the plurality of polymers has a weight average molecular weight of about 6,200, about 6,400, about 6,600, or about 6,800. In certain even further preferred embodiments, the plurality of polymers has a weight average molecular weight of about 6,400.

In other preferred embodiments, the plurality of polymers has a number average of repeat units in W of about 90 and a number average of repeat units in X of about 10. In certain embodiments, the plurality of polymers has a number average molecular weight of between 9,000 to 13,000. In certain embodiments, the plurality of polymers has a number average molecular weight of between 9,500 to 12,500. In certain embodiments, the plurality of polymers has a number average molecular weight of between 10,000 to 12,000. In preferred certain embodiments, the plurality of polymers has a number average molecular weight of between 10,500 to 11,500. In preferred certain even further embodiments, the plurality of polymers has a number average molecular weight of between 10,700 to 11,200.

In certain embodiments, the plurality of polymers has a number average molecular weight of about 9,000, about, 9,200, about 9,400, about 9,600, about 9,800, about 10,000, about 10,200, about 10,400, about 10,600, about 10,800, about 11,000, about 11,200, about 11,400, about 11,600, about 11,800, about 12,000, about 12,200, about 12,400, about 12,600, about 12,800, or about 13,000. In certain embodiments, the plurality of polymers has a number average molecular weight about 10,000, about 10,200, about 10,400, about 10,600, about 10,800, about 11,000, about 11,200, about 11,400, about 11,600, about 11,800, or about 12,000. In preferred certain embodiments, the plurality of polymers has a number average molecular weight about 10,600, about 10,800, about 11,000, about 11,200, or about 11,400. In certain even further preferred embodiments, the plurality of polymers has a number average molecular weight about 10,800, about 11,000, or about 11,200. In certain even further preferred embodiments, the plurality of polymers has a number average molecular weight about 10,900.

In certain embodiments, the plurality of polymers has a weight average molecular weight of between 12,000 to 16,000. In certain embodiments, the plurality of polymers has a weight average molecular weight of between 12,500 to 15,500. In certain preferred embodiments, the plurality of polymers has a weight average molecular weight of between 13,400 to 14,800. In certain even further preferred embodiments, the plurality of polymers has a weight average molecular weight of between 14,000 to 14,400.

In certain embodiments, the plurality of polymers has a weight average molecular weight of about 12,000, about 12,200, about 12,400, about 12,600, about 12,800, about 13,000, about 13,200, about 13,400, about 13,600, about 13,800, about 14,000, about 14,200, about 14,400, about 14,600, about 14,800, about 15,000, about 15,200, about 15,400, about 15,600, about 15,800, or about 16,000. In certain embodiments, the plurality of polymers has a weight average molecular weight of about 13,000, about 13,200, about 13,400, about 13,600, about 13,800, about 14,000, about 14,200, about 14,400, about 14,600, about 14,800, or about 15,000. In certain preferred embodiments, the plurality of polymers has a weight average molecular weight of about 13,800, about 14,000, about 14,200, about 14,400, about 14,600, or about 14,800. In certain even further preferred embodiments, the plurality of polymers has a weight average molecular weight of about 14,000, about 14,200, or about 14,400. In certain even further preferred embodiments, the plurality of polymers has a weight average molecular weight of about 14,200.

In certain embodiments, based on a number average, the ratio of repeat units comprising a hydrophilic group to repeat units comprising a hydrophobic group is from about 2:1 to about 20:1. In certain preferred embodiments, based on a number average, the ratio of repeat units comprising a hydrophilic group to repeat units comprising a hydrophobic group is about 3:1. In other preferred embodiments, the ratio of monomers, based on a number average, comprising a hydrophilic group to repeat units comprising a hydrophobic group is about 9:1.

In certain embodiments, the ratio of X:W, based on a number average, is from about 2:1 to about 20:1. In certain preferred embodiments, the ratio of X:W, based on a number average, is about 3:1. In other preferred embodiments, the ratio of X:W, based on a number average, is about 9:1.

In certain embodiments, the ratio of repeat units, based on a weight average, comprising a hydrophilic group to repeat units comprising a hydrophobic group is from about 2:1 to about 20:1. In certain preferred embodiments, based on a weight average, the ratio of repeat units comprising a hydrophilic group to repeat units comprising a hydrophobic group is about 3:1. In other preferred embodiments, the ratio of repeat units, based on a weight average, comprising a hydrophilic group to repeat units comprising a hydrophobic group is about 9:1.

In another aspect, the present disclosure provides a hierarchical structure comprising a thermoresponsive polymer, wherein the hierarchical structure has a lower critical solution pH, a lower critical solution osmolarity, a lower critical macromolecule concentration, and/or a lower critical solution temperature (LCST).

In certain embodiments, the hierarchical structure is a nanoemulsion. In certain embodiments, the hierarchical structure is a liposome. In certain embodiments, the hierarchical structure is a micelle.

In certain embodiments, the hierarchical structure is from about 10 nm to about 500 nm in diameter. In certain embodiments, the hierarchical structure is from about 20 nm to about 500 nm in diameter. In certain embodiments, the hierarchical structure is about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm or about 500 nm in diameter. In certain preferred embodiments, the hierarchical structure is about 185 nm in diameter.

In certain embodiments, the hierarchical structure further comprises at least one active agent. In certain embodiments, the active agent is covalently coupled to the polymer. In certain embodiments, the active agent is covalently coupled to the surface of the hierarchical structure. In other embodiments, the active agent is not covalently coupled to the polymer. In certain embodiments, the hierarchical structure encapsulates the active agent. In other embodiments, the hierarchical structure enmeshes the active agent. In certain embodiments, the active agent is selected from a small molecule, a protein (e.g., an antibody), a polynucleotide, and an imaging agent.

In certain embodiments, the hierarchical structure has a lower critical solution pH, a lower critical solution osmolarity, a lower critical macromolecule concentration, or LCST. In certain embodiments, the hierarchical structure has a lower critical solution pH. In certain embodiments, the hierarchical structure has a lower osmolarity. In certain embodiments, the hierarchical structure has a lower critical macromolecule concentration. In certain embodiments, the hierarchical structure has a LCST. In certain embodiments, the lower critical macromolecule concentration at about 37° C. is from about 70 to about 250 mg/mL. In certain embodiments, the LCST of the hierarchical structure is from about 30° C. to about 70° C. under the conditions present in a physiologic fluid or in a cell. In certain embodiments, the LCST of the hierarchical structure is about 35° C., about 37.5° C., about 40° C., about 42.5° C., about 45° C., about 47.5° C., about 50° C., about 52.5° C., about 55° C., 57.5° C., or about 60° C. under the conditions present in a physiologic fluid or in a cell. In certain preferred embodiments, the LCST under the conditions present in a physiologic fluid, such as blood, is below 37° C. In other preferred embodiments, the LCST under the conditions present in a physiologic fluid, such as blood, is above 37° C. In certain preferred embodiments, the LCST under the conditions present inside a cell is above 37° C. In other preferred embodiments, the LCST under the conditions present inside a cell is below 37° C.

In certain embodiments, the hierarchical structure comprises an internal hydrophilic phase. In other embodiments, the hierarchical structure comprises an internal hydrophobic phase. In certain embodiments, the hierarchical structure comprises an internal fluorous phase.

In certain embodiments, the external surface of the hierarchical structure is hydrophilic. In other embodiments, the external surface of the hierarchical structure is hydrophobic.

In yet another aspect, the present disclosure provides a hierarchical structure comprising a composition of the disclosure.

In certain embodiments, the hierarchical structure is a nanoemulsion. In certain embodiments, the hierarchical structure is a liposome. In certain embodiments, the hierarchical structure is a micelle.

In certain embodiments, the hierarchical structure is from about 10 nm to about 500 nm in diameter. In certain embodiments, the hierarchical structure is from about 20 nm to about 500 nm in diameter. In certain embodiments, the hierarchical structure is about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm or about 500 nm in diameter. In certain preferred embodiments, the hierarchical structure is about 185 nm in diameter.

In certain embodiments, the hierarchical structure further comprises at least one active agent. In certain embodiments, the active agent is covalently coupled to the polymer. In certain embodiments, the active agent is covalently coupled to the surface of the hierarchical structure. In other embodiments, the active agent is not covalently coupled to the polymer. In certain embodiments, the hierarchical structure encapsulates the active agent. In other embodiments, the hierarchical structure enmeshes the active agent. In certain embodiments, the active agent is selected from a small molecule, a protein (e.g., an antibody), a polynucleotide, and an imaging agent.

In certain embodiments, the hierarchical structure has a lower critical solution pH, a lower critical solution osmolarity, a lower critical macromolecule concentration, or LCST. In certain embodiments, the hierarchical structure has a lower critical solution pH. In certain embodiments, the hierarchical structure has a lower osmolarity. In certain embodiments, the hierarchical structure has a lower critical macromolecule concentration. In certain embodiments, the hierarchical structure has a LCST. In certain embodiments, the lower critical macromolecule concentration at about 37° C. is from about 70 to about 250 mg/mL. In certain embodiments, the LCST of the hierarchical structure is from about 30° C. to about 70° C. under the conditions present in a physiologic fluid or in a cell. In certain embodiments, the LCST of the hierarchical structure is about 35° C., about 37.5° C., about 40° C., about 42.5° C., about 45° C., about 47.5° C., about 50° C., about 52.5° C., about 55° C., 57.5° C., or about 60° C. under the conditions present in a physiologic fluid or in a cell. In certain preferred embodiments, the LCST under the conditions present in a physiologic fluid, such as blood, is below 37° C. In other preferred embodiments, the LCST under the conditions present in a physiologic fluid, such as blood, is above 37° C. In certain preferred embodiments, the LCST under the conditions present inside a cell is above 37° C. In other preferred embodiments, the LCST under the conditions present inside a cell is below 37° C.

In certain embodiments, the hierarchical structure comprises an internal hydrophilic phase. In other embodiments, the hierarchical structure comprises an internal hydrophobic phase. In certain embodiments, the hierarchical structure comprises an internal fluorous phase.

In certain embodiments, the external surface of the hierarchical structure is hydrophilic. In other embodiments, the external surface of the hierarchical structure is hydrophobic.

In yet another aspect, the present disclosure provides a hierarchical structure comprising a polymer of the disclosure.

In certain embodiments, the hierarchical structure is a nanoemulsion. In certain embodiments, the hierarchical structure is a liposome. In certain embodiments, the hierarchical structure is a micelle.

In certain embodiments, the hierarchical structure is from about 10 nm to about 500 nm in diameter. In certain embodiments, the hierarchical structure is from about 20 nm to about 500 nm in diameter. In certain embodiments, the hierarchical structure is about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm or about 500 nm in diameter. In certain preferred embodiments, the hierarchical structure is about 185 nm in diameter.

In certain embodiments, the hierarchical structure further comprises at least one active agent. In certain embodiments, the active agent is covalently coupled to the polymer. In certain embodiments, the active agent is covalently coupled to the surface of the hierarchical structure. In other embodiments, the active agent is not covalently coupled to the polymer. In certain embodiments, the hierarchical structure encapsulates the active agent. In other embodiments, the hierarchical structure enmeshes the active agent. In certain embodiments, the active agent is selected from a small molecule, a protein (e.g., an antibody), a polynucleotide, and an imaging agent.

In certain embodiments, the hierarchical structure has a lower critical solution pH, a lower critical solution osmolarity, a lower critical macromolecule concentration, or LCST. In certain embodiments, the hierarchical structure has a lower critical solution pH. In certain embodiments, the hierarchical structure has a lower osmolarity. In certain embodiments, the hierarchical structure has a lower critical macromolecule concentration. In certain embodiments, the hierarchical structure has a LCST. In certain embodiments, the lower critical macromolecule concentration at about 37° C. is from about 70 to about 250 mg/mL. In certain embodiments, the LCST of the hierarchical structure is from about 30° C. to about 70° C. under the conditions present in a physiologic fluid or in a cell. In certain embodiments, the LCST of the hierarchical structure is about 35° C., about 37.5° C., about 40° C., about 42.5° C., about 45° C., about 47.5° C., about 50° C., about 52.5° C., about 55° C., 57.5° C., or about 60° C. under the conditions present in a physiologic fluid or in a cell. In certain preferred embodiments, the LCST under the conditions present in a physiologic fluid, such as blood, is below 37° C. In other preferred embodiments, the LCST under the conditions present in a physiologic fluid, such as blood, is above 37° C. In certain preferred embodiments, the LCST under the conditions present inside a cell is above 37° C. In other preferred embodiments, the LCST under the conditions present inside a cell is below 37° C.

In certain embodiments, the hierarchical structure comprises an internal hydrophilic phase. In other embodiments, the hierarchical structure comprises an internal hydrophobic phase. In certain embodiments, the hierarchical structure comprises an internal fluorous phase.

In certain embodiments, the external surface of the hierarchical structure is hydrophilic. In other embodiments, the external surface of the hierarchical structure is hydrophobic.

In yet another aspect, the present disclosure provides a pharmaceutical composition comprising the polymer or hierarchical structure and an active agent.

In yet another aspect, the present disclosure provides a method of delivering a bioactive agent to an interior of a cell, comprising contacting the cell with the polymer or hierarchical structure of the disclosure.

In certain embodiments, the method comprises contacting the cell with the hierarchical structure of the disclosure.

In certain embodiments, the step of contacting the cell comprises administering the pharmaceutical composition of the disclosure to a subject (e.g., a human).

In certain embodiments, the hierarchical structure degrades after entering the interior of the cell.

In yet another aspect, the present disclosure provides a method administering a bioactive agent to subject, comprising administering to the subject the polymer, hierarchical structure, or pharmaceutical composition of the disclosure.

In yet another aspect, the present disclosure provides a polymer, composition, or hierarchal structure of the disclosure for use as a medicament.

In yet another aspect, the present disclosure provides a use of a polymer, composition, or hierarchal structure of the disclosure for use in the manufacture of a medicament.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution;

(19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); intravenously; subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art.

For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also be appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-30 for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, fluoroalkyl, perfluoroalkyl, perfluoroalkylalkyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

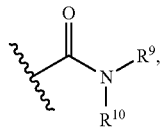

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

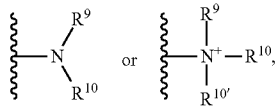

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

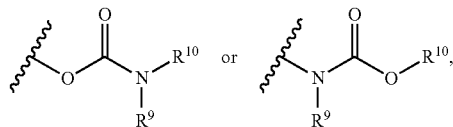

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

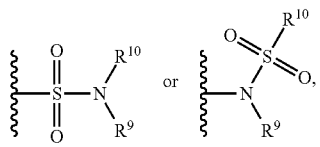

wherein R$^9$ and R$^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

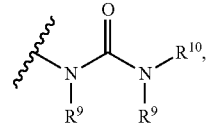

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

The term "active agent" as used herein means any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The phrase "hierarchical structure" as used herein refers to a multimer, micelle, emulsion, liposome, hydrogel, or vesicle, or mixtures thereof. The polymers disclosed herein may be formulated as hierarchical structures, for example, via self-assembly in solution (e.g., in water or certain buffers, such as phosphate buffer).

As used herein, a "number average" of a property of a polymer chain refers to the unweighted mean of that property across a polymer ensemble. Thus, for example, the "number average molecule weight" of a polymer ensemble may be expressed by the equation:

$$\overline{M}_n = \frac{\sum_i N_i M_i}{\sum_i N_i}$$

where $N_i$ is the number of molecules of molecular weight $M_i$. Weight average quantities may be determined by any suitable technique. For example, the number average molecular weight may be determined by gel permeation chromatography (also known as size exclusion chromatography) or viscometry. Other number averaged quantities may, for example, be derived from the number average molecular weight. For example, the number average of the number of repeat units in a polymer ensemble (also known as the number average degree of polymerization) may be calculated as the ratio of the number average molecular weight to the molecular weight of the repeat unit (appropriate averaged if necessary). The number average of the degree of polymerization of a polymer ensemble may also be measured directly, for example by end group analysis.

As used herein, a "weight average" of a property of a polymer chain refers to the mean of that property across a polymer ensemble, weighted by the molecular weight of the polymer chains. Thus, for example, the "weight average molecular weight" of a polymer ensemble may be expressed by the equation:

$$\overline{M}_w = \frac{\sum_i N_i M_i^2}{\sum_i N_i M_i}$$

where $N_i$ is the number of molecules of molecular weight $M_i$. Weight average quantities may be determined by any suitable technique. For example, the weight average molecular weight may be determined by light scattering, small angle neutron scattering, X-ray scattering, or sedimentation velocity. Other weight averaged quantities may, for example, be derived from the weight average molecular weight. For example, the weight average of the number of repeat units in a polymer ensemble (also known as the weight average degree of polymerization) may be calculated as the ratio of the weight average molecular weight to the molecular weight of the repeat unit (appropriate averaged if necessary).

EXAMPLES

The disclosure will be more readily understood by reference to the following examples which are included merely for purposes of illustration of certain aspects and embodiments of the disclosure, and are not intended to limit the disclosure.

Example 1: Preparation of Exemplary Polymers

General Information

Microwave reactions were performed using a CEM Discover SP microwave synthesis reactor. All reactions were performed in glass 10 mL microwave reactor vials purchased from CEM with silicone/PTFE caps. Flea micro PTFE-coated stir bars were used in the vials with magnetic stirring set to high and 15 seconds of premixing prior to the temperature ramping. All microwave reactions were carried out at 140° C. with the pressure release limit set to 250 psi (no reactions exceeded this limit to trigger venting) and the maximum wattage set to 250 W (the power applied was dynamically controlled by the microwave instrument and did not exceed this limit for any reactions).

Synthesis of Monomer (2-substituted-2-oxazolines)

2-substituted-2-oxazolines were substituted according to methods known in the art, for example, as described in Glassner, M. et al., Polym. Int., 2018, 67, 32-45; Hoogenboom, R. et al., 2005, 8(6), 659-671; and Wiesbrock, F. et al., Macromolecules, 2005, 38, 7957, the contents of which are incorporated by reference as if fully set forth herein.

Exemplary Synthesis of poly(2-oxazoline) Block Copolymers

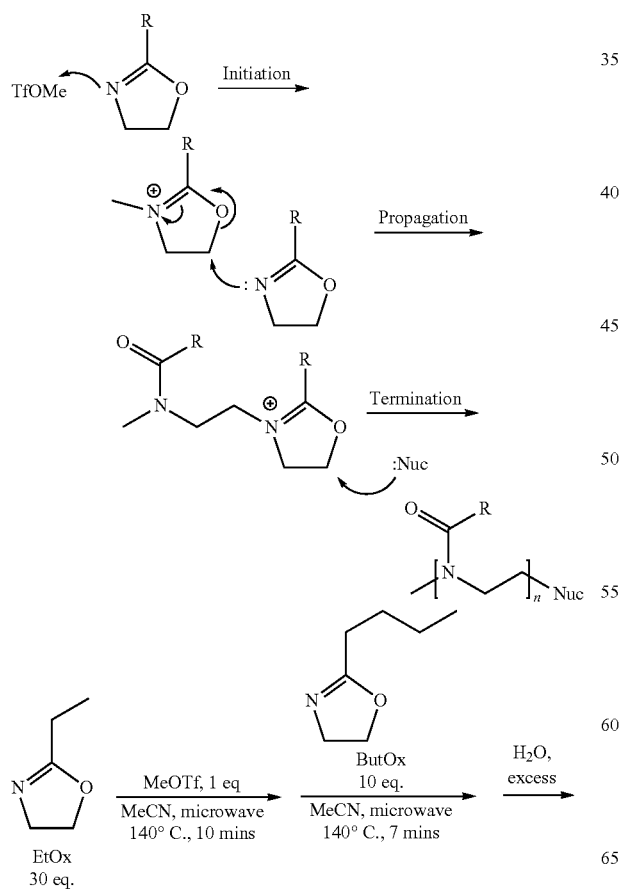

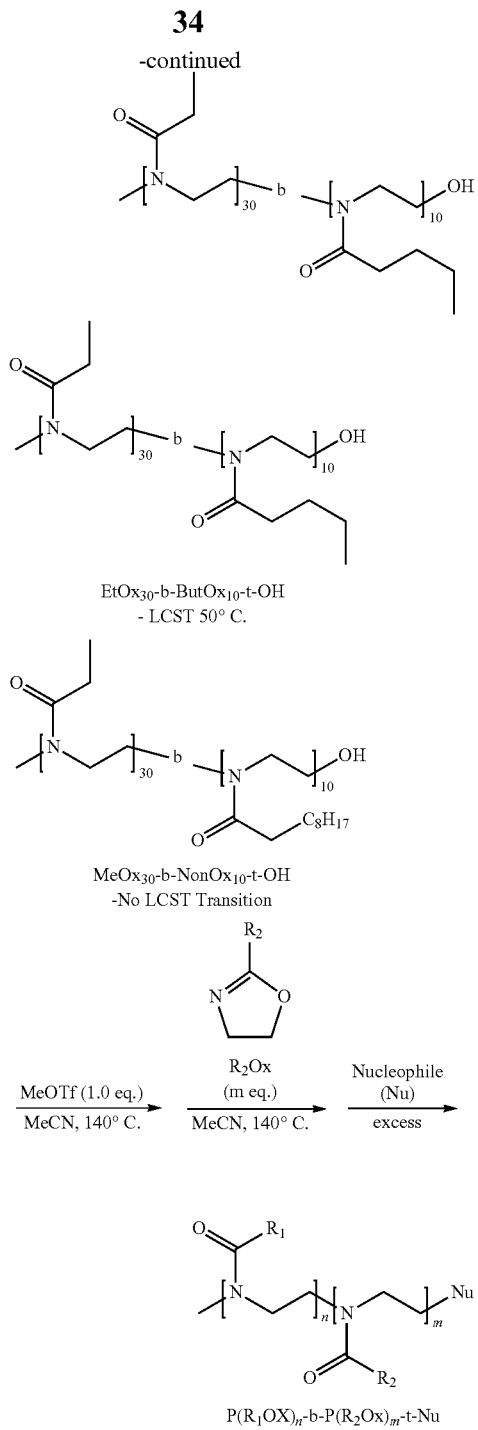

Block copolymers were synthesized through a variation of microwave-assisted cationic ring-opening polymerization according to methods known in the art, for example, as described in Glassner, M. et al., *Polym. Int.*, 2018, 67, 32-45; Hoogenboom, R. et al., *Designed Monomers and Polymers*, 2005, 8(6), 659-671; and Wiesbrock, F. et al., *Macromolecules*, 2005, 38, 7957, the contents of which are incorporated by reference as if fully set forth herein.

Briefly, to a flame dried microwave vial, MeCN (2M, 800 µL, anhydrous) and 2-ethyl-2-oxazoline (200 µL, 0.200 g, 2.02 mmol, 30.0 equiv.) were added. Following this, MeOTf (7.6 µL, 11 mg, 0.067 mmol, 1.0 equiv.) was added and the mixture was heated at 140° C. in the microwave. After 10 minutes, 2-nonyl-2-oxazoline (133 µL, 133 mg, 0.67 mmol, 10 equiv.) was added under $N_2$ and heated to 140° C. for 7 minutes, at which point the polymerization was quenched with MilliQ water (excess). The reaction mixture was evaporated to dryness to yield crude polymer as a white solid. Polymer poly(2-ethyl-2-oxazoline)-block-poly(2-nonyl-2-oxazoline) was purified by precipitation by dissolving in a minimal amount of DCM and dropwise addition to cold $Et_2O$ (20:1 v/v %), collected and evaporated to dryness (179 mg, 0.050 mmol, 62% yield). $^1$H NMR ($CDCl_3$) and lower critical solubility temperature characterization confirmed the product.

Scope of poly(2-oxazoline) Block Copolymers

The methods disclosed herein may be used to synthesize a range of polymers, such as homopolymers, diblock copolymers, triblock copolymers, and random copolymer.

Homopolymers:

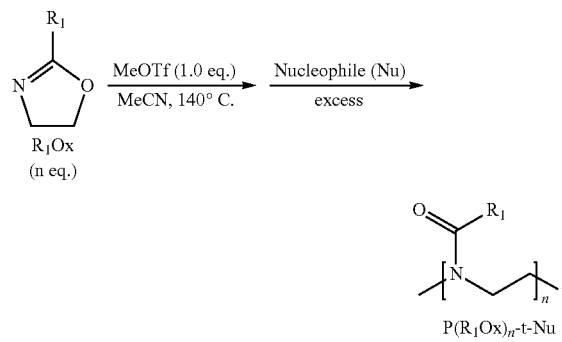

$P(R_1Ox)_n$-t-Nu $R_1Ox$ = thermoresponsive hydrophilic block (e.g. $R_1 = C_2H_5$, $CH(CH_3)_2$, $C_3H_7$, etc.)

Diblock copolymers:

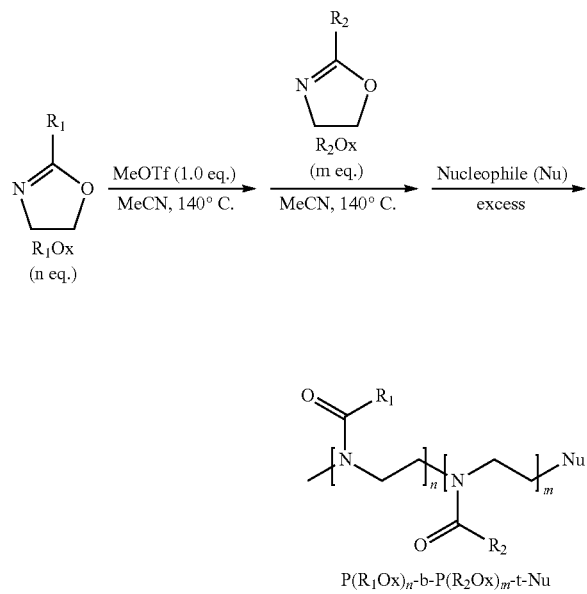

$P(R_1Ox)_n$-b-$P(R_2Ox)_m$-t-Nu $R_1Ox$ = thermoresponsive hydrophilic block (e.g. $R_1 = C_2H_5$, $CH(CH_3)_2$, $C_3H_7$, etc.)
$R_2Ox$ = hydrophobic block (e.g. $R_2 = C_8H_{17}$, $C_9H_{19}$, $C_2H_4C_6F_{13}$)

Triblock copolymers:

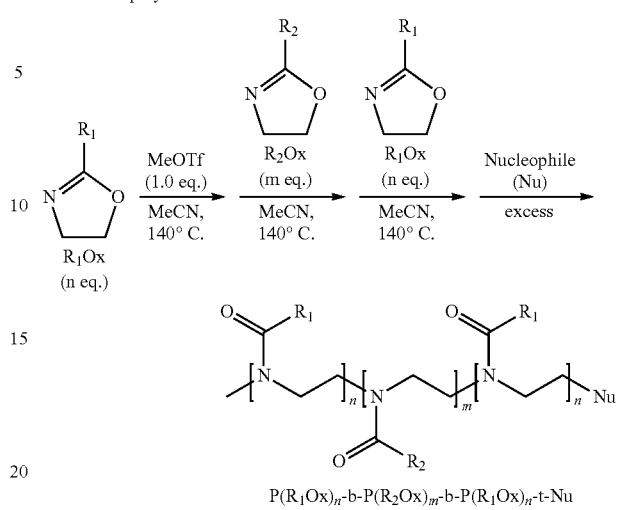

$P(R_1Ox)_n$-b-$P(R_2Ox)_m$-b-$P(R_1Ox)_n$-t-Nu $R_1Ox$ = thermoresponsive hydrophilic block (e.g. $R_1 = C_2H_5$, $CH(CH_3)_2$, $C_3H_7$, etc.)
$R_2Ox$ = hydrophobic block (e.g. $R_2 = C_8H_{17}$, $C_9H_{19}$, $C_2H_4C_6F_{13}$)

Random copolymers:

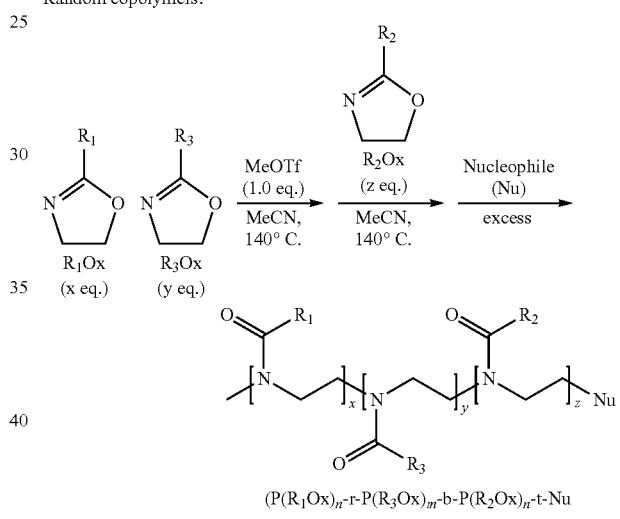

$(P(R_1Ox)_n$-r-$P(R_3Ox)_m$-b-$P(R_2Ox)_n$-t-Nu $R_1Ox$ = thermoresponsive hydrophilic block (e.g. $R_1 = C_2H_5$, $CH(CH_3)_2$, $C_3H_7$, etc.)
$R_2Ox$ = hydrophobic block (e.g. $R_2 = C_8H_{17}$, $C_9H_{19}$, $C_2H_4C_6F_{13}$)
$R_3Ox$ = functional comonomer (e.g. $(CH_2)_2CHCH_2$, $(CH_2)_3CCH$)

Exemplary Nanoemulsion Formation Procedure

Polymer surfactant (5.6 mg) was dissolved in PBS buffer pH 7.4 (200 µL) and 7:3 perfluorodecalin:perfluorotripropylamine (10 vol %, 20 µL) was added. The mixture was sonicated at 35% amplitude for 90 seconds at 0° C. on a QSonica (Q125) sonicator, oftentimes pulse sonicated (2s ON/5s OFF). Sonication was performed by lowering the probe directly at the liquid-liquid interface of the two immiscible solvents.

Exemplary Nanoemulsion Size Analysis

The bulk emulsion solution was diluted in MilliQ $H_2O$ (20 µL emulsions in 2 mL MilliQ $H_2O$) in a plastic 1 cm cuvette. Size was analyzed with a Malvern Zetasizer Nano dynamic light scattering. SOP parameters: 10 runs, 10 seconds/run, three measurements, no delay between measurements, 25° C. with 120 second equilibration time. Collection parameters: Lower limit=0.6, Upper limit=1000, Resolution=High, Number of size classes=70, Lower size limit=0.4, Upper size limit=1000, Lower threshold=0.05, Upper threshold=0.01. Data are representative of three replicate measurements. Size error bars represent the half-width at half-maximum of the measurements.

Polymer LCST Characterization

A solution of poly(2-substituted-2-oxazoline) (28 mg/ml) in MilliQ H$_2$O was made. Temperature interval measurements were then taken (1° C., 60 second equilibration, 500 nm, Jasco V-770 spectrophotometer, Jasco ETCS-761 temperature-controlled cuvette holder). Per standard technique, lower critical solubility temperature is defined as a 10% change in percent transmittance (% T).

Nanoemulsion LCST Characterization

Degradation of nanoemulsions containing poly(2-substituted-2-oxazolines) was analyzed via both dynamic light scattering (DLS) and UV-Vis analysis. From 220 μL batch of nanoemulsions, 100 μL aliquot was diluted 1:1 vol % with either PBS, MilliQ water, or solution containing additive (vide infra). Per DLS analysis, size distributions were analyzed from 20° C. to 70° C. at 5° C. intervals. Both Z-average (nm) and polydispersity (PDI) showed emulsion degradation at temperatures corresponding to surfactant LCST. Emulsion degradation was visually corroborated, showing phase separation at temperatures above the LCST. Per UV-Vis analysis, temperature interval measurements were taken (15 to 70° C., 1° C. intervals, 60 second equilibration, 500 nm, Jasco V-770 spectrophotometer, Jasco ETCS-761 temperature-controlled cuvette holder).

LCST Characterization in Varying Environments

Standard solutions of either poly(2-oxazoline)s or poly (2-oxazoline)-stabilized nanoemulsions were made with varying concentrations of macromolecules of interest. These included (i) proteins (bovine serum albumin, lysozyme, protamine) and (ii) crowding agents (Ficoll-70, Ficoll-400, Dextran-70, and PEG MW 1k, 2k, 4k, 8k, and 10k) at concentrations of 0-500 mg/mL. Both polymer and nanoemulsion LCST characterization was then carried out as described above, with dilutions corresponding to above concentrations unless otherwise specified.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of delivering a bioactive agent to an interior of a cell, comprising contacting the cell with a micelle comprising the bioactive agent and a polymer, wherein the bioactive agent is enmeshed by or encapsulated by the micelle and the polymer comprises repeat units represented by formula II:

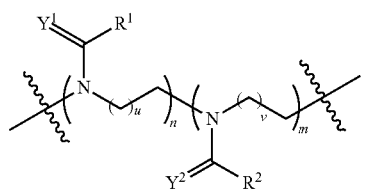

II wherein:
n is 30 or 90 and m is 10;
R$^1$ is a group that imparts hydrophilic character to the polymer;
R$^2$ is a group that imparts hydrophobic character to the polymer;
Y$^1$, Y$^2$, Y$^3$, Y$^4$, Y$^5$, Y$^6$, Y$^7$, Y$^8$, Y$^9$, Y$^{10}$, and Y$^{11}$ are each independently selected from NR$^3$, O, S, Se, P, or C(R$^3$)$_2$;
each R$^3$ is independently selected from hydrogen, alkyl, and aralkyl;
each R$^4$, R$^5$, R$^6$, R$^7$, R$^8$, R$^9$, R$^{10}$, R$^{11}$, R$^{12}$, and R$^{13}$ is independently selected from hydrogen, alkyl, cycloalkyl, arylalkyl, heteroaryl, and heterocyclyl;
u is an integer from 1 to 10; and
v is an integer from 1 to 10.

2. The method of claim 1, wherein R$^1$ is C$_1$-C$_3$ alkyl, or alkenyl.

3. The method of claim 1, wherein R$^2$ is C$_3$-C$_{20}$alkyl, cycloalkyl or aryl.

4. The method of claim 1, wherein the polymer further comprises a block Z and Z is a repeat unit represented by formula IV:

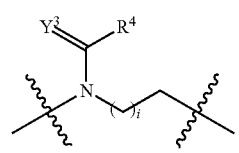

IV wherein:
Y$^3$ is selected from NR$^3$, O, or S;
R$^4$ is a linking moiety capable of participating in a 1,3-dipolar cycloaddition reaction, a hetero-Diels reaction, a nucleophilic substitution reaction, a non-aldol type carbonyl reaction, an oxidation reaction, or a click reaction; and
i is an integer from 1 to 10.

5. The method of claim 4, wherein R$^4$ is alkenyl or alkynyl.

6. The method of claim 4, wherein Z comprises from 1 to 90 repeat units.

7. The method of claim 1, wherein the micelle is from 10 nm to 500 nm in diameter.

8. The method of claim 7, wherein the micelle is from 20 nm to 500 nm in diameter.

9. The method of claim 8, wherein the micelle is 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, or 500 nm in diameter.

10. The method of claim 1, wherein the micelle encapsulates the bioactive agent.

11. The method of claim 1, wherein the micelle enmeshes the bioactive agent.

12. The method of claim 1, wherein the bioactive agent is selected from a small molecule, a protein, a polynucleotide, and an imaging agent.

13. The method of claim 1, wherein the micelle has a lower critical solution pH, a lower critical solution osmolarity, a lower critical macromolecule concentration, or LCST.

14. The method of claim 13, wherein the micelle has a lower critical solution pH.

15. The method of claim 13, wherein the micelle has a lower critical macromolecule concentration.

16. The method of claim 13, wherein the micelle has a LCST.

17. The method of claim 15, wherein the lower critical macromolecule concentration at 37° C. is 70 to 250 mg/mL.

18. The method of claim 16, wherein the LCST of the micelle is 30° C. to 70° C. under the conditions present in a physiologic fluid or in a cell.

19. The method of claim 18, wherein the LCST of the micelle is 35° C., 37.5° C., 40° C., 42.5° C., 45° C., 47.5° C., 50° C., 52.5° C., 57.5° C., or 60° C. under the conditions present in a physiologic fluid or in a cell.

20. The method of claim 19, wherein the LCST under the conditions present in a physiologic fluid is below 37° C.

\* \* \* \* \*